(12) United States Patent
Guillemont et al.

(10) Patent No.: US 9,394,295 B2
(45) Date of Patent: Jul. 19, 2016

(54) ANTIBACTERIAL HOMOPIPERIDINYL SUBSTITUTED 3,4-DIHYDRO-1H-[1,8]NAPHTHYRIDINONES

(75) Inventors: Jerôme Emile Georges Guillemont, Andé (FR); David Francis Alain Lançois, Louviers (FR); Magali Madeleine Simone Motte, Louviers (FR); Anil Koul, Edegem (BE); Wendy Mia Albert Balemans, Kalmthout (BE)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 45 days.

(21) Appl. No.: 14/237,841

(22) PCT Filed: Aug. 10, 2012

(86) PCT No.: PCT/EP2012/065729
§ 371 (c)(1),
(2), (4) Date: Feb. 7, 2014

(87) PCT Pub. No.: WO2013/021051
PCT Pub. Date: Feb. 14, 2013

(65) Prior Publication Data
US 2014/0171418 A1    Jun. 19, 2014

(30) Foreign Application Priority Data

Aug. 10, 2011    (EP) .................................... 11177115

(51) Int. Cl.
*A61K 31/55*    (2006.01)
*A61K 31/551*    (2006.01)
*C07D 471/04*    (2006.01)

(52) U.S. Cl.
CPC .................................... *C07D 471/04* (2013.01)

(58) Field of Classification Search
CPC ..... A61K 31/55; A61K 31/551; C07D 471/04
USPC .................. 514/213.01, 217.05, 217.07, 218; 540/575, 593, 597, 599
See application file for complete search history.

(56) References Cited

U.S. PATENT DOCUMENTS 4,215,123 A    7/1980    Scotese et al.

FOREIGN PATENT DOCUMENTS

| WO | WO 01/26652    | 4/2001  |
|----|----------------|---------|
| WO | WO 01/26654    | 4/2001  |
| WO | WO 01/27103    | 4/2001  |
| WO | WO 03/088897   | 10/2003 |
| WO | WO 2007/043835 | 4/2007  |
| WO | WO 2007/053131 | 5/2007  |
| WO | WO 2008/009122 | 1/2008  |
| WO | WO 2008/098374 | 8/2008  |
| WO | WO 2011/061214 | 5/2011  |

OTHER PUBLICATIONS

Bergler et al, "The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA", *European Journal of Biochemistry* (1996) 242:689-694.

Heath et al, "Enoyl-acyl carrier protein reductase (fabI) plays a determinant role in completing cycles of fatty acid elongation in *Escherichia coli*", *Journal of Biological Chemistry*(1995) 270:26538-42.

*Primary Examiner* — Brenda Coleman

(57) ABSTRACT

The present invention is related to novel compounds of formula (I) that inhibit the activity of the FabI enzyme which are therefore useful in the treatment of bacterial infections. It further relates to pharmaceutical compositions comprising these compounds, and chemical processes for preparing these compounds.

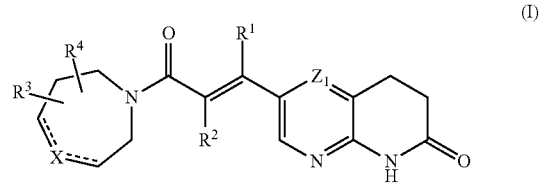

(I)

12 Claims, No Drawings

ANTIBACTERIAL HOMOPIPERIDINYL SUBSTITUTED 3,4-DIHYDRO-1H-[1,8]NAPHTHYRIDINONES

The present invention is related to novel compounds of formula (I) that inhibit the activity of the FabI enzyme which are therefore useful in the treatment of bacterial infections. It further relates to pharmaceutical compositions comprising these compounds, and chemical processes for preparing these compounds.

The compounds of the present invention are antibacterial compounds that inhibit the FabI protein, a NADH-dependent enoyl-acyl carrier protein (ACP) reductase enzyme in the fatty acid biosynthesis pathway. Fatty acid synthase (FAS) is involved in the overall biosynthetic pathway of saturated fatty acids in all organisms, but the structural organization of FAS varies considerably among them. The distinctive characteristics of FAS of vertebrates and yeasts are that all enzymatic activities are encoded on one or two polypeptide chains, and that the acyl carrier protein (ACP) exists in the form of a complex. In contrast, in bacterial FAS, each of synthetic steps is catalyzed by a distinct, mono-functional enzyme and the ACP is a discrete protein. Therefore, it is possible to selectively inhibit bacterial FAS by blocking one of the synthetic steps using an inhibitory agent. NADH-dependent enoyl-ACP reductase (Fab I) is involved in the last step of the four reaction steps involved in each cycle of bacterial fatty acid biosynthesis. Thus, the FabI enzyme is the biosynthetic enzyme in the overall synthetic pathway of bacterial fatty acid biosynthesis.

The FabI enzyme has been shown to constitute an essential target in major pathogens such as *E. Coli* (Heath et al. *J. Biol. Chem.* 1995, 270, 26538; Bergler et al. *Eur. J. Biochem.* 2000, 275, 4654). Hence, compounds that inhibit FabI may be useful as antibacterials.

Compounds having FabI enzyme inhibitory activity have been disclosed in WO-01/26652, WO-01/26654, and WO-01/27103. Substituted naphthyridinone compounds having FabI inhibitory activity have been disclosed in WO-03/088897, WO-2007/043835 and WO-2008/098374. International patent application WO 2007/053131 also discloses various naphthyridone compounds for potential use as FabI inhibitors. However, none of these documents discloses a compound in which there is a cyclic amino group directly attached to a carbonyl moiety that is a to an alkene. International patent application WO 2011/061214 also discloses various compounds for potential use as FabI inhibitors. However, this document does not specifically disclose inter alia compounds in which there is a 7-membered nitrogen-containing cyclic group optionally containing a double bond.

The present invention relates to a compound of formula (I)

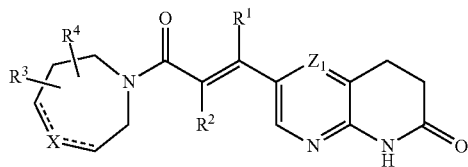

(I)

wherein $\overset{\backslash\backslash}{X}\text{\textemdash\textemdash}$ represents a radical wherein only one of the two ----- bonds represents either a single bond or a double bond and the other ----- bond then represents a single bond;

X represents carbon or nitrogen, and when X represent nitrogen then both ----- bonds represent a single bond;

$Z_1$ represents CH or N;

$R^1$ is hydrogen, $C_{1-4}$alkyl or halo;

$R^2$ is hydrogen, $C_{1-4}$alkyl or halo;

$R^3$ is hydrogen, $C_{1-6}$alkyl, hydroxy or halo;

$R^4$ is hydrogen, $C_{1-6}$alkyl, halo, aryl, heteroaryl, $C_{1-6}$alkyl substituted with aryl, or $C_{1-6}$alkyl substituted with heteroaryl;

and when the substituents $R^3$ and $R^4$ are located on adjacent positions said $R^3$ and $R^4$ may be taken together to form a radical of formula =CH—CH=CH—CH= with the proviso that X represents carbon and the two ----- bonds represent a single bond;

aryl is phenyl; phenyl substituted with one, two or three substituents each individually selected from halo, hydroxy, $C_{1-4}$alkyl, polyhalo$C_{1-4}$alkyl, $C_{1-4}$alkyloxy, polyhalo$C_{1-4}$alkyloxy, cyano, nitro, and amino;

heteroaryl is furanyl, thiophenyl, pyrrolyl, pyrazolyl, imidazolyl, isoxazolyl, thiazolyl, triazolyl, tetrazolyl, isothiazolyl, thiadiazolyl, oxadiazolyl, pyridinyl, pyridazinyl, pyrimidinyl, pyrazinyl, benzo[1,3]dioxolyl, benzofuranyl, benzothiazolyl, indolyl, 2,3-dihydro-1H-indolyl, tetrahydrothiophenyl, or quinolinyl;

wherein each heteroaryl may be substituted with one or two substituents each independently selected from halo, cyano, $C_{1-4}$alkyl, $C_{1-4}$alkyloxy, $C_{1-4}$alkylcarbonyl, or phenyl;

or a pharmaceutically acceptable acid addition salt thereof.

As used in the foregoing definitions:

halo is generic to fluoro, chloro, bromo and iodo;

$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like;

$C_{1-6}$alkyl is meant to include $C_{1-4}$alkyl and the higher homologues thereof having 5 or 6 carbon atoms, such as, for example, 2-methylbutyl, pentyl, hexyl and the like;

polyhalo$C_{1-4}$alkyl is defined as polyhalo substituted $C_{1-4}$alkyl (as hereinabove defined) substituted with 2 to 6 halogen atoms such as difluoromethyl, trifluoromethyl, trifluoroethyl, and the like.

As used in the description, whenever the term "compound of formula (I)" is used, it is meant to include also the pharmaceutically addition salts the compounds of formula (I) are able to form and the solvates the compounds of formula (I) or the pharmaceutically acceptable acid addition salts of compounds of formula (I) are able to form.

The definition of "compounds of formula (I)" inherently includes all stereoisomers of the compound of formula (I) either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a disubstituted cycloalkyl group, the substituents may be in the cis or trans configuration. Therefore, the invention includes enantiomers, diastereomers, racemates, cis isomers, trans isomers and mixtures thereof.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

The terms "stereoisomers" or "stereochemically isomeric forms" hereinbefore or hereinafter are used interchangeably.

The absolute stereochemical configuration of the compounds of formula (I) and of the intermediates used in their preparation may easily be determined by those skilled in the art while using well-known methods such as, for example, X-ray diffraction.

Some of the compounds of formula (I) may also exist in their tautomeric form. Such forms although not explicitly indicated in the above formula are intended to be included within the scope of the present invention.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria.

Compounds of formula (I) that may be mentioned include those in which:
(i) $Z_1$ represents CH, and hence the compound of formula I represents the following:

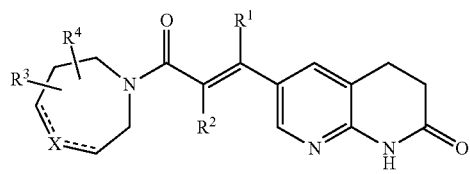

wherein
(ii) when $R^1$ or $R^2$ represent halo, then they are preferably F or Cl;
(iii) $R^1$ represents hydrogen or $C_{1-4}$alkyl; and/or
(iv) $R^2$ represents hydrogen or $C_{1-4}$alkyl.

Interesting compounds of formula (I) are those compounds of formula (I) wherein one or more of the following restrictions apply:
a) $R^1$ and $R^2$ represent hydrogen; or
b) $R^3$ represents hydrogen; or
c) $R^3$ represents $C_{1-4}$alkyl or halo; or
d) $R^4$ represents halo, aryl, heteroaryl or $C_{1-4}$alkyl substituted with aryl; or
e) $R^3$ and $R^4$ are located on adjacent positions and taken together to form a radical of formula =CH—CH=CH—CH= with the proviso that X represents carbon and the two ----- bonds represent a single bond; and
f) heteroaryl is thiophenyl, pyrrolyl, thiazolyl or triazolyl.

A first group of compounds are the compounds of formula (I)

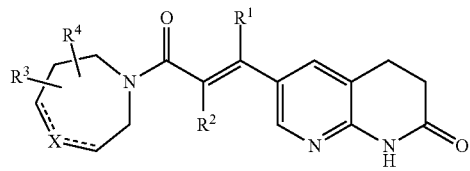

wherein $X\text{-----}$ represents a radical wherein only one of the two ----- bonds represents either a single bond or a double bond and the other ----- bond then represents a single bond;
X represents carbon or nitrogen, and when X represent nitrogen then both ----- bonds represent a single bond;
$R^1$ is hydrogen;
$R^2$ is hydrogen;
$R^3$ is hydrogen, $C_{1-6}$alkyl, or halo;
$R^4$ is halo, aryl, heteroaryl, or $C_{1-6}$alkyl substituted with aryl; and when the substituents $R^3$ and $R^4$ are located on adjacent positions said $R^3$ and $R^4$ may be taken together to form a radical of formula =CH—CH=CH—CH= with the proviso that X represents carbon and the two ----- bonds represent a single bond;
aryl is phenyl; phenyl substituted with one or two substituents each individually selected from halo, $C_{1-4}$alkyl, polyhalo$C_{1-4}$alkyl, $C_{1-4}$alkyloxy, and polyhalo$C_{1-4}$alkyloxy;
heteroaryl is thiophenyl, pyrrolyl, thiazolyl or triazolyl;
or a pharmaceutically acceptable acid addition salt thereof.

Compounds of formula (I) that may be mentioned include those in which X represents C, the two ----- bonds represents single bonds and $R^3$ and $R^4$ are present and located on adjacent positions, and taken together to form a radical of formula =CH—CH=CH—CH=. However, compounds of formula (I) that are particularly preferred include those in which:

X represents C and one of the two ----- bonds represents a double bond (and the other represents a single bond); or X represents N (in which case both the ----- bonds represent single bonds), and hence the following X-containing rings are particularly preferred:

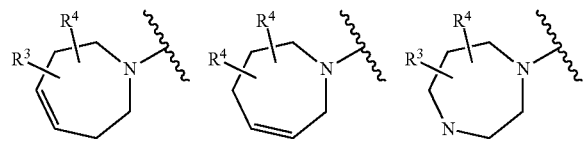

In this instance it is preferred that adjacent $R^3$ and $R^4$ groups are not taken together to form a radical.

In compounds of formula (I), it is preferred that:
(i) There is at least one $R^3$ or $R^4$ substituent present that does not represent hydrogen;
(ii) One of $R^3$ and $R^4$ (e.g. $R^3$) represent hydrogen, halo, $C_{1-3}$alkyl or hydroxy and the other one of $R^3$ and $R^4$ (e.g. $R^4$) represents a substituent other than hydrogen;
(iii) $R^3$ represents hydrogen, $C_{1-4}$ alkyl (e.g. methyl) or halo (e.g. fluoro) and most preferably represents hydrogen (i.e. $R^3$ is essentially not present);
(iv) $R^4$ represents a substituent other than hydrogen (i.e. there is an $R^4$ substituent that is present, and does not represent hydrogen);
(v) $R^4$ represents a substituent other than hydrogen, which is attached to X, in which any of the above can be taken together or in combination. For instance, (iii), (iv) and/or (v) may be taken in combination to provide the particularly preferred compounds of formula (I) below:

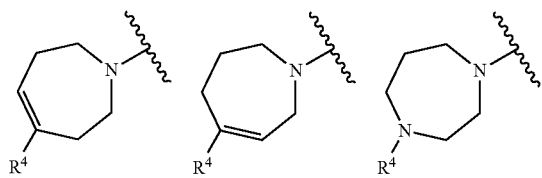

in which $R^4$ represents a substituent other than hydrogen. The most preferred X-containing rings in the compounds of formula (I) are:

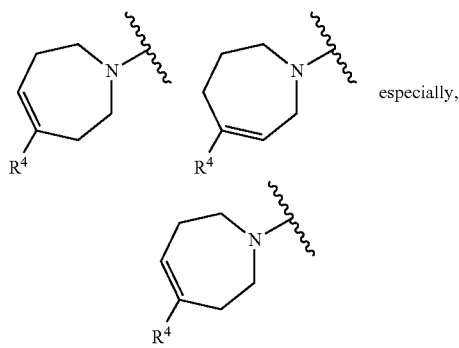

especially, in which $R^4$ represents a substituent other than hydrogen. Particularly preferred substituents that $R^4$ (here and elsewhere) may represent include:

(i) optionally substituted aryl;
(ii) optionally substituted heteroaryl;
(iii) $C_{1-6}$alkyl substituted by aryl or heteroaryl (which latter two aryl and heteroaryl groups are themselves optionally substituted as defined herein).

It is particularly preferred that the $R^4$ group contains an aromatic moiety, and hence (i), (ii) and (iii) above are particularly preferred).

In the case when $R^4$ represents (i) above, then the aryl group is preferably phenyl, which group may be unsubstituted or substituted by one or two (e.g. one) substituent selected from halo (e.g. chloro, fluoro), $C_{1-4}$alkyl (e.g. methyl), polyhalo$C_{1-4}$alkyl (e.g. —$CF_3$), $C_{1-4}$alkyloxy (e.g. —$OCH_3$), polyhalo$C_{1-4}$alkyoxy (e.g. —$OCF_3$).

In the case when $R^4$ represents (ii) above, then the heteroaryl group is preferably a monocyclic 5- or 6-membered ring containing one to four heteroatoms (e.g. one or two heteroatoms), so forming e.g. a thiazolyl (e.g. 2-thiazolyl), thienyl (e.g. 2-thienyl), pyrazolyl (e.g. 1- or 2-pyrazolyl), triazolyl (e.g. 1,2,3-triazol-1-yl) or pyrrolyl (e.g. 1-pyrrolyl).

In the case where $R^4$ represents (iii) above, then preferably the $C_{1-6}$alkyl group is methyl, i.e. —$CH_3$, which alkyl moiety is substituted with aryl (e.g. phenyl, such as unsubstituted phenyl).

Most preferably, the $R^4$ group represents (i) or (ii) above, i.e. aryl or heteroaryl. Even more preferably the $R^4$ group represents (i) above, especially unsubstituted phenyl.

It is stated hereinbefore that the following X-containing rings are particularly preferred:

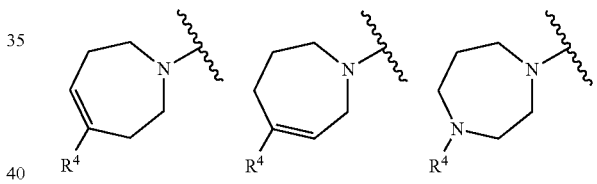

and particularly those in which $R^4$ is as defined above. Such compounds which contain either a $N(R^4)$ moiety or a $C(R^4)$ moiety adjacent a double bond may be beneficial. This is because the shape of the nitrogen atom (e.g. being more planar in nature, as compared to a $CR^4$ moiety that is not adjacent a double bond) or the presence of the double bond in the X-containing ring may help to orient the $R^4$ group (if present) such that the compound overall (e.g. in view of the $R^4$ substituent's orientation) displays better/improved binding properties to the FabI bacterial enzyme. Hence, these compounds of the invention may be advantageous in the sense that the presence of the double bond may lead to improved binding to/inhibition of the FabI enzyme.

Consequently the compounds of the invention may be advantageous compounds (e.g. compared to known compounds) by virtue of these properties which may consequentially lead to better potency, efficacy, etc.

Compounds of formula (I) can generally be prepared by reacting an intermediate of formula (II) with an intermediate of formula (III), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof.

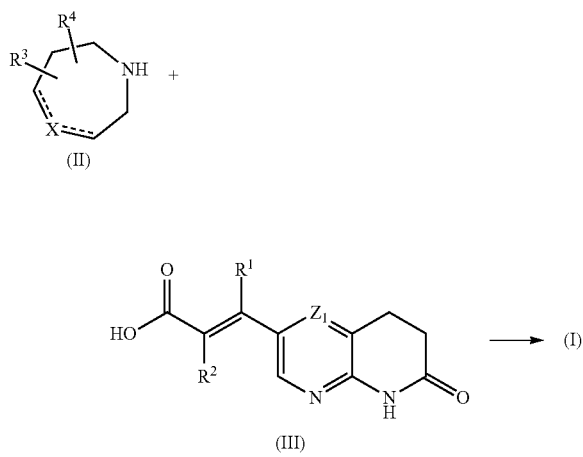

It may be convenient to activate the carboxylic acid of formula (III) by adding an effective amount of a reaction promoter. Non-limiting examples of such reaction promoters include carbonyldiimidazole, N,N'-dicyclohexyl-carbodiimide or 1-(3-dimethylaminopropyl)-3-ethylcarbodiimide, hydroxybenzotriazole, benzotriazolyl-oxytris(dimethylamino)-phosphonium hexafluorophosphate, tetrapyrrolidino-phosphonium hexafluorophosphate, bromotripyrrolidinophosphonium hexafluoro-phosphate, or a functional derivative thereof.

Compounds of formula (I) can also be prepared by reacting an intermediate of formula (II) with an intermediate of formula (IV), wherein Y represents hydroxy or halo. The reaction can be performed in a reaction-inert solvent such as, for example, dichloromethane or dimethylformamide and optionally in the presence of a suitable base such as, for example, diisopropylethyl-amine (DIPEA).

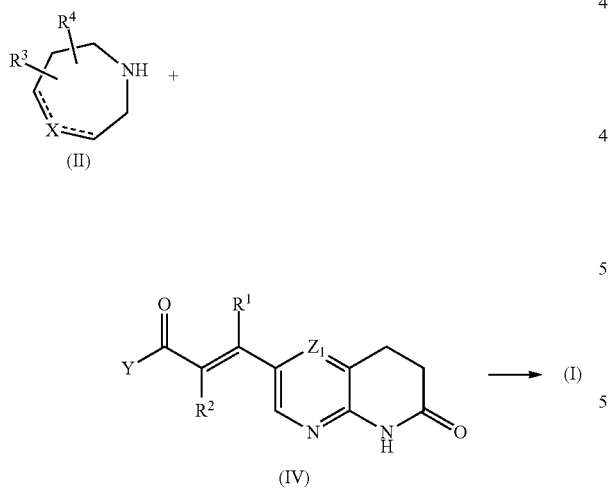

The starting materials and some of the intermediates are known compounds and are commercially available or may be prepared according to conventional reaction procedures generally known in the art.

Compounds of formula (I) can also be prepared by reacting an intermediate of formula (V) with an intermediate of formula (VI),

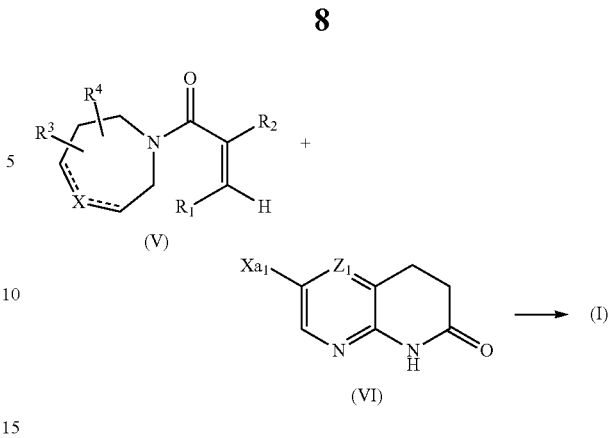

wherein $X_{a1}$ represents a suitable leaving group such as a suitable halo group (e.g. chloro, iodo and, especially, bromo) and the other integers are as hereinbefore defined, under reaction suitable reaction conditions, for example under metal catalyst coupling reaction conditions (e.g. precious metal coupling reaction conditions, wherein the precious metal is e.g. palladium-based), in particular under Heck reaction conditions using preferably a palladium-based catalyst such as palladium acetate, tetrakis-(triphenylphosphione)palladium(0), bis(triphenylphosphine)palladium(II) dichloride, [1,1'-bis(diphenylphosphino)ferrocene]palladium(II) dichloride or the like (preferably, the catalyst is palladium acetate), for instance optionally in the presence of a suitable solvent (e.g. acetonitrile or the like), base (e.g. an amine base such as N,N-diisopropyl-amine or the like), and a ligand (e.g. triphenylphosphine, tri-O-tolylphosphine or the like). The reaction may be performed in a sealed tube and/or in a microwave.

The starting materials and some of the intermediates are known compounds and are commercially available or may be prepared according to conventional reaction procedures generally known in the art.

Intermediates of formula (II-a), defined as intermediates of formula (II) wherein X represents carbon and $R^4$ is located at the 4-position of the homopiperidinyl ring, can be prepared according to the following general reaction scheme.

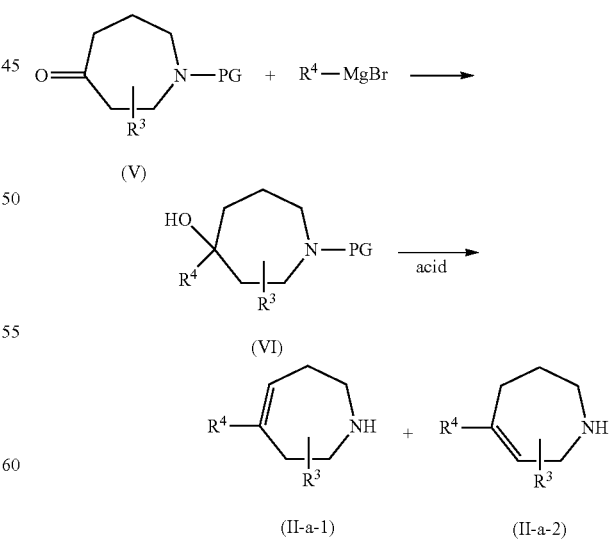

In the above reaction scheme, radical PG in intermediates (V) and (VI) is a nitrogen protecting group such as e.g. tert-butyloxycarbonyl that can easily be removed under acidic conditions. The organomagnesium reagent R⁴—MgBr can be obtained using art known organometallic reactions such as the Grignard reaction.

For the compounds in which $Z_1$ represents CH, intermediates (IV) and (VI) may be prepared as described herein, or according to conventional reaction procedures generally known in the art. For the corresponding intermediates in which $Z_1$ represents N, this may also be the case. However, such compounds may also be prepared in accordance with the following scheme:

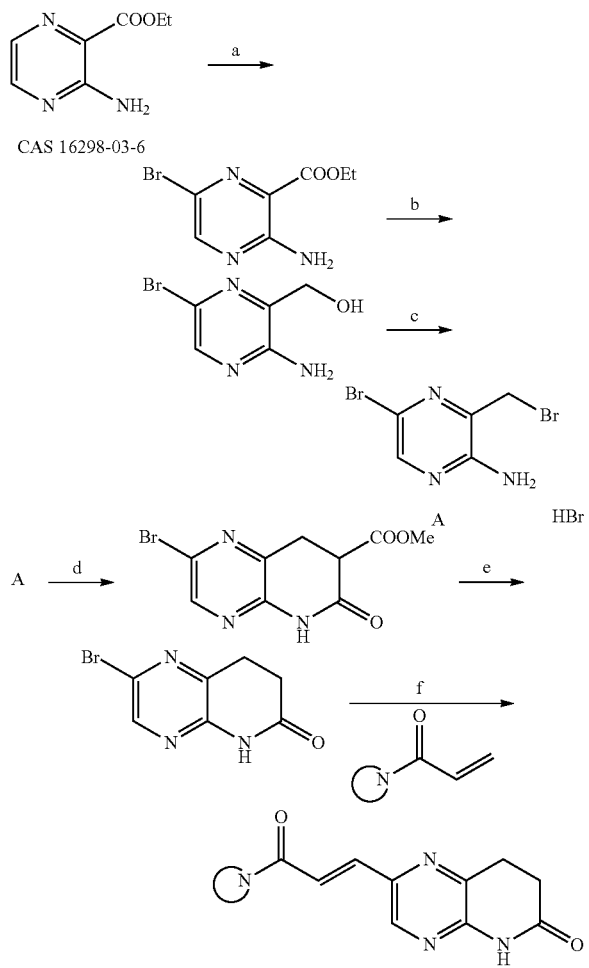

Conditions:
a) NBS, ACN, reflux, 3 h, 70%; b) LiAlH₄ 1M in THF, THF, 5° C. to RT, o.n., 20%; c) PBr₃, DCM, RT, o.n., 90%; f) dimethyl malonate, NaOMe in MeOH, MeOH, RT, o.n., 25%; g) NaOH, MeOH, reflux, 4 h, HCl, reflux, o.n.; h) DIEA, Pd(OAc)₂, tri-O-tolylphosphine, ACN, DMF, μw, 180° C., 25 min.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds described herein are inhibitors of the FabI enzyme, as demonstrated in Pharmacological Example 1. In view of these FabI enzyme inhibiting properties the compounds described herein are useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Additionally, the compounds may be useful in combination with known antibiotics.

Therefore the present invention also relates to compounds of formula (I) for use as a medicine especially for use in treating bacterial infections, in particular bacterial infections caused by a bacterium that expresses a FabI enzyme. Subsequently the present compounds may be used for the manufacture of a medicine for treatment of bacterial infections, in particular bacterial infections caused by a bacterium that expresses a FabI enzyme.

Further, the present invention provides a method of treating bacterial infections which comprises administering to a subject in need thereof a FabI enzyme inhibiting compound of formula (I).

A subject in need of treatment has a bacterial infection or has been exposed to an infectious bacterium, the symptoms of which may be alleviated by administering a therapeutically effective amount of the compounds of the present invention. For example, a subject in need of treatment can have an infection for which the compounds of formula (I) can be administered as a treatment. In another example, a subject in need of treatment can have an open wound or burn injury, for which the compounds of formula (I) can be administered as a prophylactic. Typically a subject will be treated for an existing bacterial infection.

A subject can have a bacterial infection caused by *Bacillus anthracis*, *Citrobacter* sp., *Escherichia coli*, *Francisella tularensis*, *Haemophilus influenza*, *Listeria monocytogenes*, *Moraxella catarrhalis*, *Mycobacterium tuberculosis*, *Neisseria meningitidis*, *Proteus mirabilis*, *Proteus vulgaris*, *Salmonella* sp., *Serratia* sp., *Shigella* sp., *Stenotrophomonas maltophilia*, *Staphylococcus aureus*, or *Staphylococcus epidermidis*. Preferably, the subject is treated (prophylactically or therapeutically) for a bacterial infection caused by a bacterium that expresses a FabI enzyme.

The term "treating" and "treatment", as used herein, refers to curative, palliative and prophylactic treatment, including reversing, alleviating, inhibiting the progress of, or preventing the disease, disorder or condition to which such term applies, or one or more symptoms of such disease, disorder or condition.

A "therapeutically effective amount" of a compound of the present invention is the quantity which, when administered to a subject in need of treatment, improves the prognosis of the subject, e.g. delays the onset of and/or reduces the severity of one or more of the subject's symptoms associated with a bacterial infection. The amount of the disclosed compound to be administered to a subject will depend on the particular disease, the mode of administration, and the characteristics of the subject, such as general health, other diseases, age, sex, genotype, body weight and tolerance to drugs. The skilled person will be able to determine appropriate dosages depending on these and other factors.

The compounds may be tested in one of several biological assays to determine the concentration of compound which is required to have a given pharmacological effect.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevio side sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of antibacterial diseases linked to the inhibition of the FabI enzyme will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

Compounds of formula (I) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

For instance, compounds of formula (I) may have the advantage that they have a good or an improved thermodynamic solubility (e.g. compared to compounds known in the prior art; and for instance as determined by a known method and/or a method described herein). Compounds of formula (I) may also have the advantage that they have a broad spectrum of activity against antibacterials (e.g. a broader spectrum of antibacterial activity compared to compounds known in the prior art; and for instance as determined by known tests and/or tests described herein). Compounds of formula (I) may also have the advantage that they have good or improved in vivo pharmacokinetics and oral bioavailability. They may also have the advantage that they have good or improved in vivo efficacy. For instance, the compounds of the invention may adaptable for intravenous formulation/dosing and hence may exhibit an improved in vivo efficacy when administered intravenously.

Compounds of formula (I) may surprisingly have the above-mentioned advantages or may be surprisingly comparable to compounds known in the prior art. In particular, it may be surprising that the compounds of formula (I) by virtue of the presence of the relatively large 7-membered X-containing ring have advantageous or even comparable properties. Further, particular compounds of formula (I) may exhibit further such advantages (such as those mentioned hereinbefore), for instance the compounds in which the X-containing ring contains NR$^4$ and in particular those in which it contains a CR$^4$ moiety (e.g. in which X is CR$^4$), which is adjacent to a double bond. Any of these further advantageous properties may be attributed to the presence of the moieties NR$^4$ or CR$^4$ adjacent to a double bond.

EXPERIMENTAL PART

"DMF" is defined as N,N-dimethylformamide, "DCM" or "CH$_2$Cl$_2$" is defined as dichloromethane, "MeOH" is defined as methanol, "EtOH" is defined as ethanol, "MgSO$_4$" is defined as magnesium sulfate, and "THF" is defined as tetrahydrofuran; HATU is 1-[bis(dimethylamino)methylene]-1H-1,2,3-triazolo[4,5-b]pyridinium 3-oxide hexafluorophosphate; AcOEt or EtOAc is ethyl acetate; DIPEA is diisopropylethylamine; EDCI is defined as N-(ethylcarbonimidoyl)-N,N-dimethyl-1,3-propane-diamine monohydrochloride; HOBT means 1-hydroxy-1H-benzotriazole; K$_2$CO$_3$ means potassium carbonate; NH$_4$OH is defined as ammonium hydroxide; NH$_4$Cl is defined as ammonium chloride; N$_2$ is nitrogen gas; and TFA means trifluoroacetic acid.

A. Synthesis of the Intermediates

Example A.1 a) Preparation of

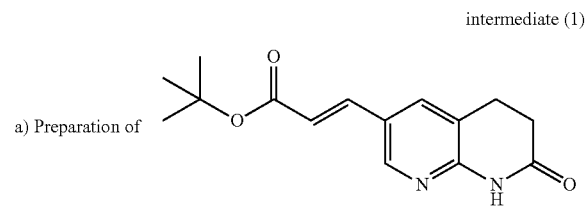 [SMILES: CC(C)(C)OC(=O)/C=C/c1cnc2c(c1)CCC(=O)N2]

intermediate (1)

A solution of 6-bromo-3,4-dihydro-1H-[1,8]naphthyridin-2-one (1.0 g, 4.4 mmol), tert-butyl acrylate (2.56 ml, 17.62 mmol) and N,N-diisopropylethylamine (1.46 ml, 8.81 mmol) in acetonitrile (20 ml) and DMF (7 ml) was stirred and degassed with nitrogen gas for 10 minutes. Tri-o-tolylphosphine (0.27 g, 0.88 mmol) and palladium (II) acetate (47% on Pd) (0.099 g, 0.44 mol) were added and the resulting mixture was microwaved (1600 W, 180° C., 35 minutes). The reaction mixture was evaporated till dryness, taken up in a mixture of DCM/methanol (8/2) (50 ml), filtered through a short pad of celite and washed with DCM. The organic layer was washed with water, dried over MgSO$_4$, filtered and evaporated to dryness. The residue was taken up in cold ethanol (10 ml) and stirred at 5° C. for 5 minutes, the precipitate was filtered off, washed with cold ethanol (3 ml) and dried under vacuum to yield 950 mg intermediate (1).

b) Preparation of 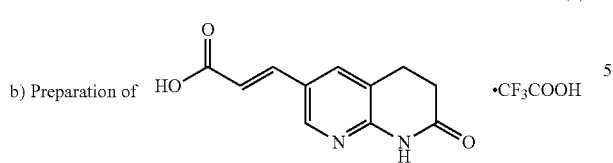 intermediate (2)

Intermediate (1) (4.1 g, 14.95 mmol) was dissolved in a mixture of trifluoroacetic acid (23.2 ml) in DCM (41 ml). The reaction was stirred at room temperature for 30 minutes. The reaction mixture was concentrated under reduced pressure. The resulting solid was triturated with diethyl ether, filtered off and dried under vacuum to yield 3.97 g of intermediate (2).

c) Preparation of 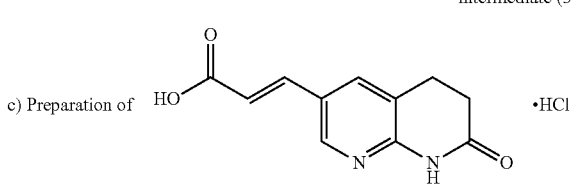 intermediate (3)

Intermediate (2) was triturated overnight in a mixture of HCl in dioxane (4 M, 48 ml), the solid was filtered off, washed with diethyl ether and dried under vacuum to give 3.7 g of intermediate (3).

Example A.2 a) Preparation of 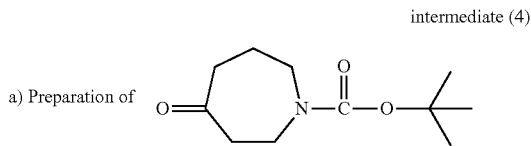 intermediate (4)

A mixture of N-benzylhexahydroazepin-4-one hydrochloride (25.0 g, 104.3 mmol), di-tert-butyl dicarbonate (25.0 g, 114.7 mmol) and Pearlman's catalyst (4.46 g, 31.3 mmol) in EtOAc (550 ml) and triethylamine (17.4 ml, 125.13 mmol) was hydrogenated at room temperature overnight in a Parr shaker. The reaction mixture was filtered through a short pad of Celite®, the cake was washed with EtOAc, the filtrate was washed with water then brine, dried (MgSO$_4$) and evaporated till dryness to give 23.4 g of intermediate (4).

b) Preparation of 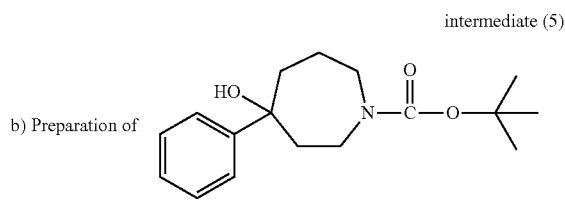 [SMILES: CC(C)(C)OC(=O)N1CCCC(O)(c2ccccc2)CC1] intermediate (5)

Reaction under N$_2$. Phenylmagnesium chloride (93.8 ml, 169 mmol) was added dropwise to a solution of intermediate (4) (30 g, 141 mmol) in THF (300 ml) at 0° C. then the mixture was stirred 3 hours at 5° C. NH$_4$Cl 10% aqueous and EtOAc were added, the organic layer was separated, washed with water and brine, dried (MgSO$_4$) and evaporated till dryness to give 39.2 g of intermediate (5).

c) Preparation of 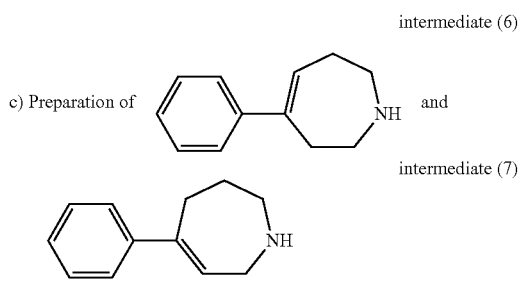

intermediate (6)

and intermediate (7)

A solution of intermediate (5) (38.85 g, 133.3 mmol) in HCl (35% in water, 200 ml) was stirred at room temperature for 1 hour. The reaction mixture was poured out into crushed ice and K$_2$CO$_3$ solid was added portionwise (until pH=9-10), then it was extracted twice with DCM. The organic layer were gathered, washed with water, dried (MgSO$_4$) and evaporated until dryness. The residue was purified by preparative liquid chromatography on (silicagel 20-45 μm, 1000 g, mobile phase (1% NH$_4$OH, 93% DCM, 7% MeOH)). The pure fractions were collected and the solvent was evaporated to yield intermediate (6) and intermediate (7).

Example A.3 a) Preparation of 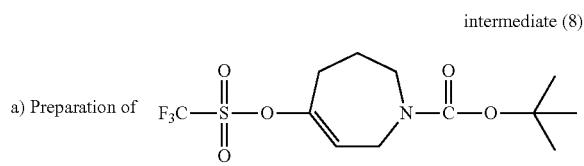 [SMILES: CC(C)(C)OC(=O)N1CC=C(OS(=O)(=O)C(F)(F)F)CCC1] intermediate (8)

Reaction under N$_2$. n-Butyllithium 1.6M in hexane (6.35 ml, 9.31 mmol) was added dropwise at −20° C. to a solution of diisopropylamine (1.43 ml, 10.2 mmol) in THF (15 ml) then the mixture was stirred at −20° C. for 20 minutes. A solution of intermediate (4) (1.9 g, 8.46 mmol) in THF (20 ml) was then added at −78° C. and the resulting mixture was stirred for 30 minutes at −78° C. A solution of 2-[N,N-bis (trifluoromethyl-sulfonyl)-amino]-5-chloropyridine (3.8 g, 9.31 mmol) in THF (10 ml) was added at −78° C. then the mixture was allowed to reach room temperature and was stirred overnight and concentrated. The residue was purified by normal phase column chromatography (silicagel 20-45 μm, 450 g, mobile phase (80% heptane, 20% ethyl acetate)). The pure fractions were collected and the solvent was evaporated to give 1.34 g of intermediate (8).

b) Preparation of 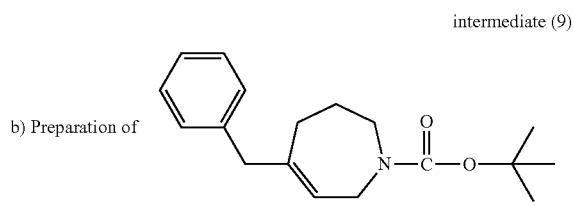 [SMILES: CC(C)(C)OC(=O)N1CC=C(Cc2ccccc2)CCC1] intermediate (9)

Reaction under N$_2$. A solution of intermediate (8) (0.24 g, 0.695 mmol) in THF (2 ml) and benzylzinc bromide in THF (0.5 M, 3.34 ml, 1.67 mmol) was degassed with nitrogen bubbling for 10 minutes then 1,1'-bis(diphenylphosphino)ferrocenedichloro-palladium(II) (0.102 g, 0.139 mmol) was added. The mixture was microwaved during 20 minutes, cooled to room temperature, water and ethyl acetate were added, the mixture was filtered through a short pad of celite, the organic layer was separated, washed with water then brine, dried (MgSO$_4$) and evaporated till dryness. The residue was purified by flash chromatography over a short silica gel cartridge with a mixture of heptane to heptane/EtOAc 90/10). The pure fractions were collected and evaporated to dryness to yield 0.11 g of intermediate (9).

c) Preparation of intermediate (10)

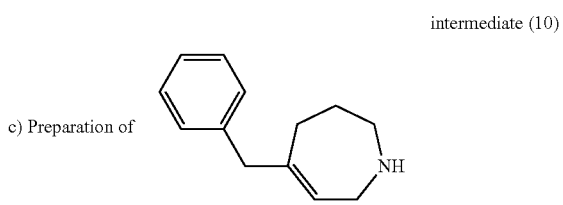 [SMILES: C1=C(Cc2ccccc2)CCCNC1]

A mixture of intermediate (9) (0.11 g, 0.383 mmol) and TFA (0.3 ml) in DCM (2 ml) was stirred at room temperature for 30 minutes then the reaction mixture was poured out into K$_2$CO$_3$ (10% aqueous solution) and extracted with DCM. The organic layer was separated, washed with water, dried (MgSO$_4$) and evaporated till dryness to yield 0.058 g of intermediate (10).

Example A.4 a) Preparation of intermediate (11)

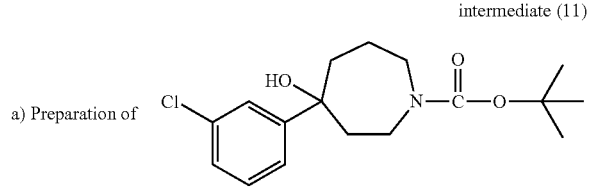 [SMILES: CC(C)(C)OC(=O)N1CCCC(O)(c2cccc(Cl)c2)CC1]

Reaction under N$_2$. 3-Chlorophenylmagnesium bromide (100 ml, 50.0 mmol) was added dropwise to a solution of intermediate (4) (8.9 g, 41.7 mmol) in THF (90 ml) at 0° C. then the mixture was stirred 3 hours at 5° C. NH$_4$Cl (10% aqueous solution) and EtOAc were added, the organic layer was separated, washed with water and brine, dried (MgSO$_4$) and evaporated till dryness. The residue was carried out by flash chromatography over a silica gel cartridge [15-40 μm, heptane/EtOAc 80/20 to heptane/EtOAc 60/40)]. The pure fractions were collected and evaporated to dryness to yield 4.4 g of intermediate (11).

intermediate (12)

b) Preparation of

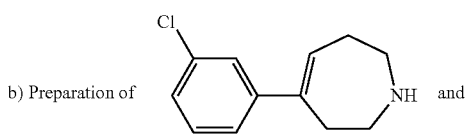
and

-continued intermediate (13)

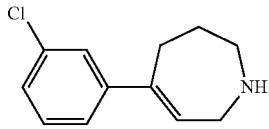

A solution of intermediate (11) (4.4 g, 13.5 mmol) in HCl in water (35%, 22 ml) was stirred at room temperature for 1 hour. The reaction mixture was poured out into crushed ice and K$_2$CO$_3$ solid was added portionwise (until pH=9-10), then it was extracted twice with DCM. The organic layer were gathered, washed with water, dried (MgSO$_4$) and evaporated until dryness. The aqueous layer was evaporated, taken up in DCM and filtered. It was gathered with the first extract and evaporated till dryness. The residue was carried out by flash chromatography over silica gel (15-40 μm, 90 g, from DCM to DCM/MeOH/NH$_4$OH: 90/10/0.5). The pure fractions were collected and evaporated to dryness. The residue was purified by preparative liquid chromatography on [silicagel 15-40 μm, 300 g, mobile phase (0.5% NH$_4$OH, 90% DCM, 10% MeOH)].

The pure fractions were collected and the solvent was evaporated to give 1 g of intermediate (12) and 0.4 g of intermediate (13).

Example A.5 intermediate (14)

a) Preparation of

Reaction under N$_2$. n-Butyllithium in hexane (1.6 M, 3.52 ml, 5.63 mmol) was added dropwise at −78° C. to a solution of thiazole (0.366 ml, 5.16 mmol) in diethyl ether (5 ml) and the mixture was stirred for 30 minutes. A solution of intermediate (4) (1.0 g, 4.69 mmol) in diethyl ether (5 ml) was added then the mixture stirred and allowed to reach room temperature for 2 hours. Water and EtOAc were added, the organic layer was separated, washed with water then brine, dried (MgSO$_4$) and evaporated till dryness. The residue was purified by preparative liquid chromatography (silicagel 15-40 μm, 25 g, mobile phase (70% heptane, 30% EtOAc)) to give 1.05 g of intermediate (14).

intermediate (15)

b) Preparation of

and intermediate (16)

Intermediate (14) (710 mg, 2.38 mmol) and HCl concentrated (2 mL) in acetonitrile (6 mL) were stirred at reflux 2 days. The solvent was evaporated. Water and DCM were added. K$_2$CO$_3$ powder was added to basify the aqueous layer and the organic layer was removed. The aqueous layer was extracted again with DCM after saturation of the aqueous layer with K$_2$CO$_3$. The combined organic layers were concentrated and the residue was purified and separated by column chromatography over silica gel (15-40 µm, 25 g), yielding 137 mg of intermediate (15) and 65 mg of intermediate (16).

Example A.6 a) Preparation of

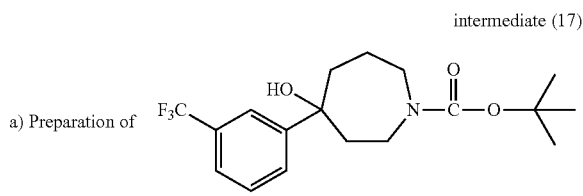 [SMILES: CC(C)(C)OC(=O)N1CCCC(O)(c2cccc(C(F)(F)F)c2)CC1]

intermediate (17)

Reaction under N$_2$. 3-(Trifluoromethyl)phenylmagnesium bromide (1.4 g, 5.6 mmol into 10 ml diethyl ether) was added dropwise to a solution of intermediate (4) (1 g, 4.69 mmol) in THF (15 ml) at 0° C. then the mixture was stirred 3 hours at 5° C. NH$_4$Cl (10% aqueous solution) and EtOAc were added, the organic layer was separated, washed with water and brine, dried (MgSO$_4$) and evaporated till dryness. Purification was carried out by flash chromatography over silica gel (40 g, heptane/EtOAc from 85/15). Pure fractions were collected and concentrated, yielding 520 mg of intermediate (17).

b) Preparation of

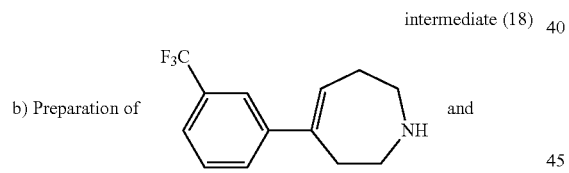

intermediate (18)

and

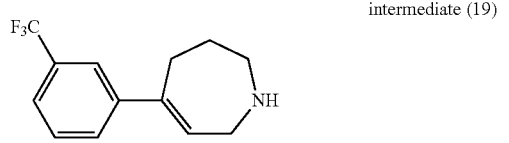

intermediate (19)

A solution of intermediate (17) (400 mg, 1.13 mmol) in HCl (37% in water, 15 ml) was stirred for 30 minutes at reflux then cooled to room temperature. The reaction mixture was poured out into crushed ice and K$_2$CO$_3$ solid was added portionwise (until pH=9-10), then it was extracted twice with DCM. The organic layer were gathered, washed with water, dried (MgSO$_4$) and evaporated until dryness. The residue was purified by preparative liquid chromatography on (silicagel 5 µm, 150×30.0 mm, mobile phase (gradient from 0.2% NH$_4$OH, 98% DCM, 2% MeOH to 1.2% NH$_4$OH, 88% DCM, 12% MeOH)). The pure fractions were collected and the solvent was evaporated to yield 140 mg of intermediate (18) and 42 mg of intermediate (19).

Example A.7 a) Preparation of

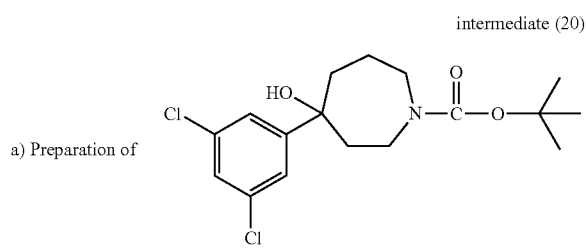 [SMILES: CC(C)(C)OC(=O)N1CCCC(O)(c2cc(Cl)cc(Cl)c2)CC1]

intermediate (20)

Reaction under N$_2$. 3-Chloro-5-fluorophenylmagnesium bromide (5M in THF) (14.1 mL, 7 mmol) was added dropwise to a solution of intermediate (4) (1 g, 4.7 mmol) in THF (20 ml) at 0° C. then the mixture was stirred 3 hours at 5° C. NH$_4$Cl (10% aqueous solution) and EtOAc were added, the organic layer was separated, washed with water and brine, dried (MgSO$_4$) and evaporated till dryness. Purification was carried out by flash chromatography over silica gel (40 g, heptane/EtOAc from 85/15). Pure fractions were collected and concentrated to yield 900 mg of intermediate (20).

b) Preparation of

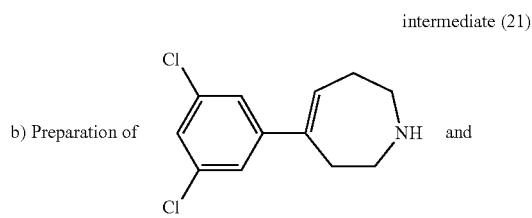

intermediate (21)

and

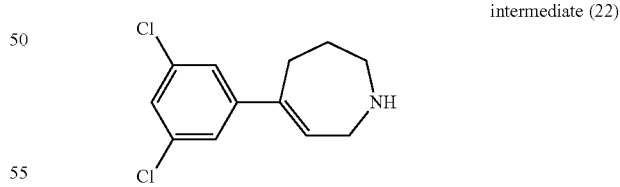

intermediate (22)

A solution of intermediate (20) (900 mg, 2.5 mmol) in HCl (37% in water, 30 ml) was stirred for 30 minutes at reflux then cooled to room temperature. The reaction mixture was poured out into crushed ice and K$_2$CO$_3$ solid was added portionwise (until pH=9-10), then it was extracted twice with DCM. The organic layer were gathered, washed with water, dried (MgSO$_4$) and evaporated until dryness. The residue was purified by preparative liquid chromatography on (silicagel 5 µm 150×30.0 mm). mobile phase (gradient from 0.2% NH$_4$OH, 98% DCM, 2% MeOH to 1% NH$_4$OH, 90% DCM, 10%

MeOH). Two fractions were collected and the solvent was evaporated to yield 290 mg of intermediate (21) and 80 mg of intermediate (22).

Example A.8 a) Preparation of
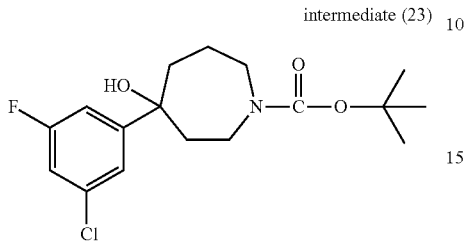
intermediate (23)

Reaction under N₂. 3-Chloro-5-fluorophenylmagnesium-bromide (0.5 M in THF, 18.7 mL, 9.37 mmol) was added dropwise to a solution of intermediate (4) (1 g, 4.7 mmol) in THF (20 ml) at 0° C. then the mixture was stirred 3 hours at 5° C. NH₄Cl (10% aqueous solution) and EtOAc were added. The organic layer was separated, washed with water and brine, dried (MgSO₄) and evaporated till dryness. Purification was carried out by flash chromatography over silica gel (40 g, heptane/EtOAc from 85/15). The pure fractions were collected and the solvent was evaporated to yield 650 mg of intermediate (23).

b) Preparation of
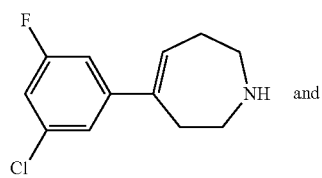
intermediate (24)
and
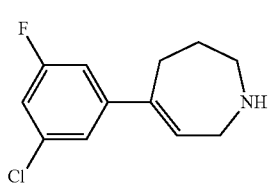
intermediate (25)

A solution of intermediate (23) (800 mg, 2.33 mmol) in HCl (37% in water, 25 ml) was stirred for 30 minutes at reflux and then cooled to room temperature. The reaction mixture was poured out into crushed ice and K₂CO₃ solid was added portionwise (until pH=9-10), then it was extracted twice with DCM. The organic layers were gathered, washed with water, dried (MgSO₄) and evaporated until dryness. The crude product was purified by preparative liquid chromatography on (silicagel 5 μm 150×30.0 mm, mobile phase (gradient from 0.2% NH₄OH, 98% DCM, 2% MeOH to 1% NH₄OH, 90% DCM, 10% MeOH)). Two fractions were collected and the solvent was evaporated to yield 325 mg of intermediate (24) and 90 mg of intermediate (25).

Example A.9 a) Preparation of
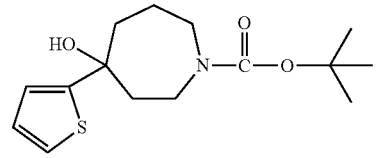
intermediate (26)

Reaction under N₂. n-Butyllithium (1.6 M in hexane, 10.55 ml, 16.88 mmol) was added dropwise at −78° C. to a solution of 2-bromothiophene (1.5 ml, 15.47 mmol) in diethyl ether (7.5 ml) then the mixture was stirred for 30 minutes. A solution of intermediate (4) (3 g, 14.07 mmol) in diethyl ether (7.5 ml) was added. The mixture stirred and allowed to reach room temperature for 2 hours. Water and EtOAc were added, the organic layer was separated, washed with water then brine, dried (MgSO₄) and evaporated till dryness. The residue was purified by preparative liquid chromatography on (silicagel 15-40 μm, 90 g, mobile phase (80% heptane, 20% EtOAc)). The pure fractions were collected and the solvent was evaporated to yield 2.65 g of intermediate (26).

b) Preparation of
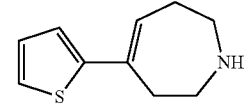
intermediate (27)

Intermediate (26) (6.3 g, 21.18 mmol) and HCl concentrated (15 mL) in acetic acid (45 mL) were stirred at reflux for 45 minutes. Solvents were evaporated. Water and DCM were added. K₂CO₃ powder was added to basify and the organic phase was removed. The aqueous phase was saturated with K₂CO₃ powder and extracted with a solvent mixture of DCM with methanol (95/5). Both organic phases were combined, evaporated to dryness and the residue was purified by column chromatography over silica gel (15-40 μm, 100 g) with a solvent mixture of DCM/methanol/NH₄OH (92/7/1), yielding intermediate (27).

Example A.10 a) Preparation of
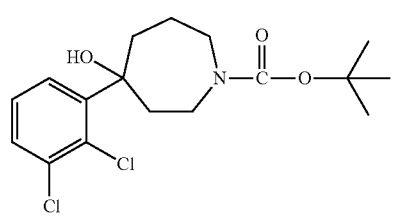
intermediate (29)

Reaction under N₂. Bromo(2,3-dichlorophenyl)-magnesium (3.75 g, 15 mmol into 20 ml diethyl ether) was added dropwise to a solution of intermediate (4) (2.1 g, 10 mmol) in THF (20 ml) at 0° C. then the mixture was stirred 3 hours at 5° C. NH₄Cl (10% aqueous solution) and EtOAc were added, the organic layer was separated, washed with water and brine, dried (MgSO₄) and evaporated till dryness. The crude product was crystallized from heptane/EtOAc 80/20 and air dried, yielding 700 mg of intermediate (29).

b) Preparation of

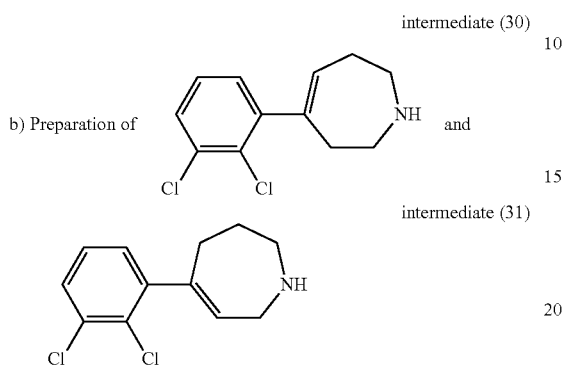

intermediate (30)

and intermediate (31)

A solution of intermediate (29) (700 mg, 1.694 mmol) in HCl (37% in water, 20 ml) was stirred for 30 minutes at reflux then cooled to room temperature. The reaction mixture was poured out into crushed ice and K₂CO₃ solid was added portionwise (until pH=9-10), then it was extracted twice with DCM. The organic layer were gathered, washed with water, dried (MgSO₄) and evaporated until dryness. The crude product was purified by preparative liquid chromatography on (silicagel 5 μm 150×30.0 mm, mobile phase (gradient from 0.2% NH₄OH, 98% DCM, 2% MeOH to 1.1% NH₄OH, 89% DCM, 11% MeOH)). The pure fractions were collected and the solvent was evaporated, yielding intermediate (30) and a second fraction. The second fraction was purified by preparative liquid chromatography on (silicagel 5 μm 150×30.0 mm, mobile phase (gradient from 0.2% NH₄OH, 98% DCM, 2% MeOH to 1.1% NH₄OH, 89% DCM, 11% MeOH)). The pure fractions were collected and the solvent was evaporated, yielding intermediate (31).

Example A.11 a) Preparation of

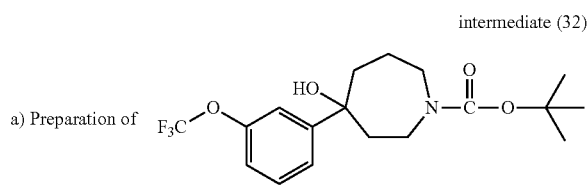 [SMILES: CC(C)(C)OC(=O)N1CCCC(O)(c2cccc(OC(F)(F)F)c2)CC1]

intermediate (32)

Reaction under N₂. Bromo[3-(trifluoromethoxy)phenyl]-magnesium (1.1 g, 4.15 mmol into 10 ml diethyl ether) was added dropwise to a solution of intermediate (4) (0.6 g, 2.77 mmol) in THF (10 ml) at 0° C. then the mixture was stirred 3 hours at 5° C. NH₄Cl (10% aqueous solution) and EtOAc were added, the organic layer was separated, washed with water and brine, dried (MgSO₄) and evaporated till dryness. Purification was carried out by flash chromatography over silica gel (40 g, heptane/EtOAc from 80/20). Pure fractions were collected and concentrated, yielding 250 mg of intermediate (32).

b) Preparation of

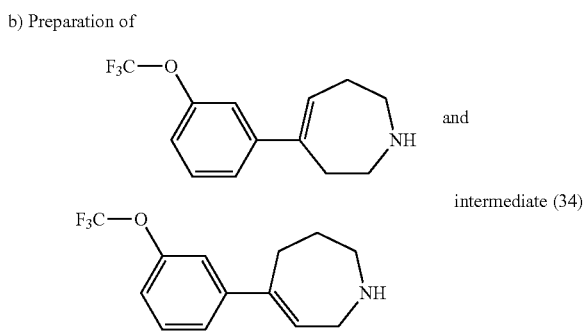

intermediate (33)

and intermediate (34)

A solution of intermediate (32) (240 mg, 0.639 mmol) in HCl (37% in water, 10 ml) was stirred for 30 minutes at reflux then cooled to room temperature. The reaction mixture was poured out into crushed ice and K₂CO₃ solid was added portionwise (until pH=9-10), then it was extracted twice with DCM. The organic layer were gathered, washed with water, dried (MgSO₄) and evaporated until dryness. The residue (136 mg) was purified by column chromatography over silica gel (15-40 μm, 25 g) with a solvent mixture of DCM/methanol/acetonitrile (92/7/1) to give 86 mg of intermediate (33) and 33 mg of intermediate (34).

Example A.12 a) Preparation of

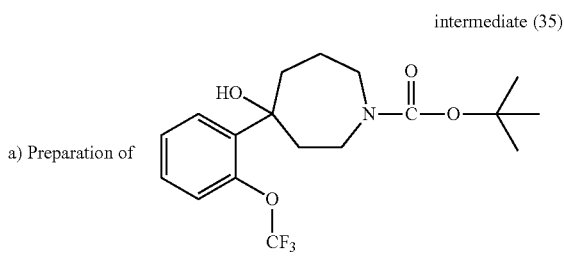 [SMILES: CC(C)(C)OC(=O)N1CCCC(O)(c2ccccc2OC(F)(F)F)CC1]

intermediate (35)

Reaction under N₂. Bromo[2-(trifluoromethoxy)phenyl]-magnesium (3.63 g, 13.7 mmol into 15 ml diethyl ether) was added dropwise to a solution of intermediate (4) (1.95 g, 9.1 mmol) in THF (20 ml) at 0° C. then the mixture was stirred 3 hours at 5° C. NH₄Cl (10% aqueous solution) and EtOAc were added, the organic layer was separated, washed with water and brine, dried (MgSO₄) and evaporated till dryness. Purification was carried out by flash chromatography over silica gel (40 g, heptane/EtOAc from 80/20). Pure fractions were collected and concentrated, yielding 550 mg of intermediate (35).

b) Preparation of

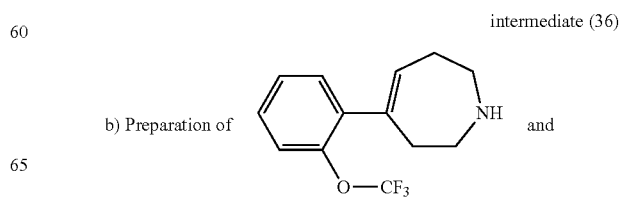

intermediate (36)

and

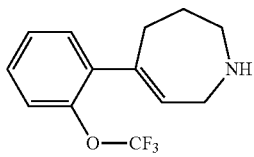

intermediate (37)

Intermediate (35) (450 mg, 1.2 mmol) and HCl concentrated (1.5 mL) in acetic acid (4.5 mL) were stirred at reflux overnight. Solvents were evaporated. Water and DCM were added. $K_2CO_3$ powder was added to basify. The organic layer was removed and evaporated and the crude product (350 mg) was purified by preparative liquid chromatography on (silicagel 5 μm 150×30.0 mm, mobile phase (gradient from 0.2% $NH_4OH$, 98% DCM, 2% MeOH to 1.2% $NH_4OH$, 88% DCM, 12% MeOH)). Two fractions were collected and the solvent was evaporated, yielding 140 mg of intermediate (36) and 63 mg of intermediate (37).

Example A.13

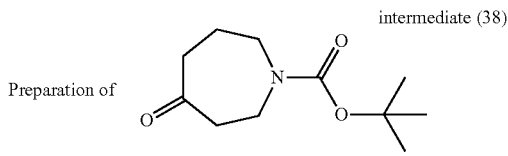

intermediate (38)

Preparation of

Hexahydro-1-(phenylmethyl)-4H-azepin-4-one, hydrochloride (56 g, 233 mmol) was added to $Na_2CO_3$ (saturated, aqueous solution, 1000 mL) and EtOAc (1000 mL). The mixture was stirred for 30 minutes. The organic layer was separated, the water layer was extracted with EtOAc (1000 mL). The combined organic layers were dried over $Na_2SO_4$, filtrated and the filtrate's solvent was evaporated. The residue and tert-butyl dicarbonate (66 g, 300 mmol) in EtOAc (800 mL) was hydrogenated at room temperature (0.4 MPa) with $Pd(OH)_2$ (15 g) as a catalyst. After uptake of hydrogen (1 equivalent), the catalyst was filtered off and the filtrate was evaporated. The residue was purified by column chromatography over silica gel (eluent: petroleum ether/EtOAc 3/1). The product fractions were collected and the solvent was evaporated, yielding 49 g of intermediate (38).

Example A.14

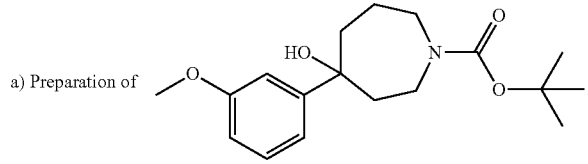

intermediate (39)

a) Preparation of

Mg (0.34 g, 14 mmol), a few drops of a solution of 1-bromo-3-methoxy-benzene (1.1 ml, 9.28 mmol) in THF (5 mL) and iodine (0.01 g) in THF (30 mL) was introduced in to an anhydrous three-necked flask equipped with a nitrogen supply, a funnel, and a reflux condenser. The mixture was gently heated until the reaction started, then the rest solution of 1-bromo-3-methoxy-benzene was added dropwise at a rate which maintained reflux. Agitation was continued until the iodine completely disappeared (about 1 hour). Then the mixture was cooled to 0° C. The solution of intermediate (38) (2.0 g, 9.38 mmol) in THF (10 ml) was added to the mixture. The reaction mixture was stirred at ice-bath, then warmed to room temperature. The reaction mixture was quenched with saturated $NH_4Cl$ (20 mL) and stirred at room temperature overnight. The organic layer was separated, the water layer was extracted with EtOAc (3×50 mL). The combined organic layers were dried over $Na_2SO_4$, filtrated and the filtrate's solvent was evaporated. The residue was purified by column chromatography over silica gel (eluent: petroleum ether/ EtOAc 10/1). The product fraction were collected and the solvent was evaporated, yielding 2.3 g of intermediate (39).

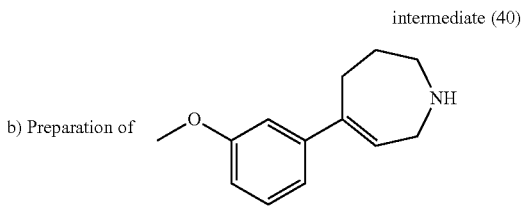

intermediate (40)

b) Preparation of

To a solution of intermediate (39) (2.0 g, 6.5 mmol) in DCM (30 mL) was added drop wise TFA (20 mL) at 0° C. After the addition, the mixture was stirred for 2 hour at room temperature. The reaction mixture was concentrated (<35° C.). The mixture was partitioned with brine (20 mL), $Na_2CO_3$ (5 g) and EtOAc (20 mL), the water layer was extracted with EtOAc (3×20 mL). The combined organic layer was dried over $Na_2SO_4$, filtrated and the solvent was evaporated. The residue was purified by column chromatography over silica gel (eluent: DCM/MeOH 30/1). The pure fractions were collected and the solvent was evaporated, yielding 0.2 g of intermediate (40).

The following compounds were made using the same procedure as Example A.14 whereby 1-methoxy-3-methyl-benzene was replaced by 1-bromo-2-methyl-benzene, 2-bromo-4-fluoro-1-methoxy-benzene, 1-bromo-4-chloro-benzene, 1-bromo-2-methoxy-benzene, 2-bromo-4-fluoro-1-methyl-benzene, 1-bromo-4-methoxy-benzene, 1-bromo-3-methoxy-benzene, 1-bromo-3-chloro-benzene or 1-bromo-2-chloro-benzene respectively.

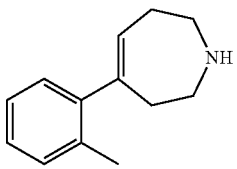

intermediate (41)

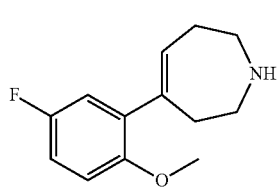

intermediate (42)

-continued intermediate (43)
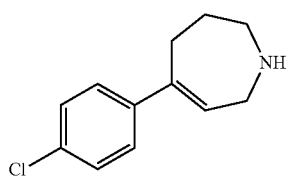

intermediate (44)
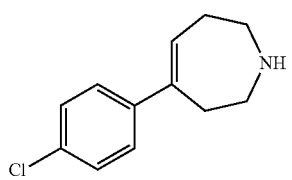

intermediate (45)
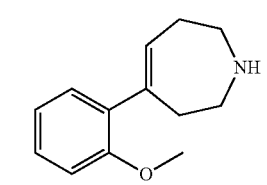

intermediate (46)
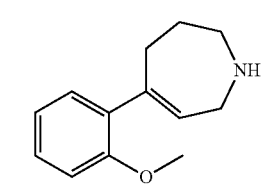

intermediate (47)
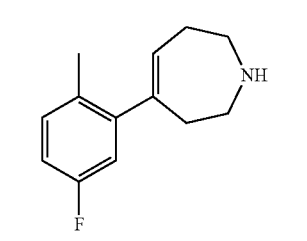

intermediate (48)
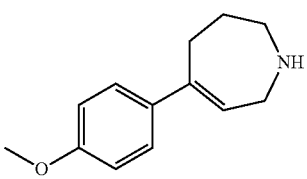

intermediate (49)
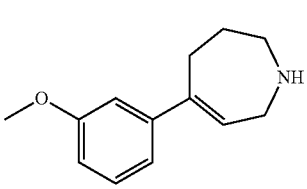

intermediate (50)
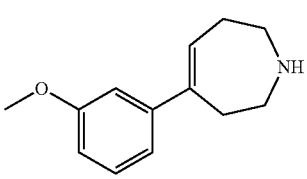

-continued intermediate (51)
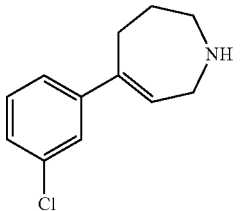

intermediate (52)
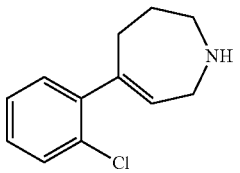

Example A.15 a) Preparation of intermediate (53)

A solution of 1-bromo-2-fluoro-benzene (1.48 g, 8.5 mmol) in anhydrous THF (50 mL) was stirred under nitrogen at −78° C. for 30 minutes and then n-butyllithium (2.5 M in hexane, 3.5 mL, 10.1 mmol) was added dropwise −78° C. over 5 to 10 minutes and the formed mixture was stirred for 30 minutes. Then intermediate (38) (1.5 g, 101 mmol) in THF (10 mL) was added via syringe. After addition, the cooling bath was removed. The reaction mixture was stirred for 1 hour, then quenched with 1N HCl (200 ml), The mixture was extracted with DCM (3×100 mL). The combined organic layers were separated and dried over anhydrous $Na_2SO_4$, then filtered and concentrated in vacuum. The residue was purified by column chromatograph over silica gel (eluent: petroleum ether/EtOAc 10/1). The pure fractions were collected and the solvent was evaporated, yielding 1.54 g of intermediate (53).

b) Preparation of intermediate (54)

To a solution of intermediate (53) (1 g, 3.2 mmol) in DCM (20 mL) was added drop wise TFA (15 mL) at 0° C. After the addition, the mixture was stirred for 2 hours at room temperature. The reaction mixture was concentrated (<35° C.). The mixture was partitioned with brine (5 mL), $Na_2CO_3$ (5 g) and EtOAc (50 mL), the water layer was extracted with EtOAc (3×50 mL). The combined organic layers were dried over $Na_2SO_4$, filtrated and the solvent was evaporated. The residue was purified by column chromatography over silica gel (eluent: DCM/MeOH 30/1). The pure fractions were collected and the solvent was evaporated, yielding 0.6 g of intermediate (54).

The following compounds were made using the same procedure as Example A.15 whereby 1-bromo-2-fluoro-benzene was replaced by 2-bromo-1-fluoro-3-methoxy-benzene or 2-bromo-1,4-dimethyl-benzene respectively.

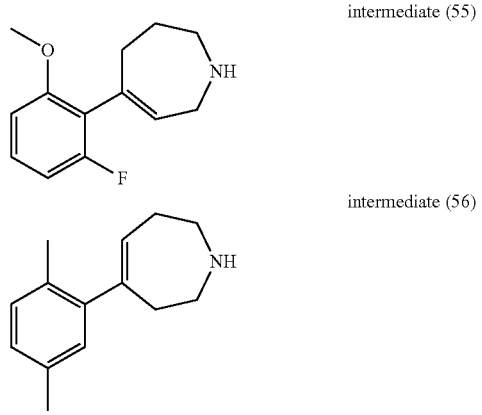

intermediate (55)

intermediate (56)

Example A.16

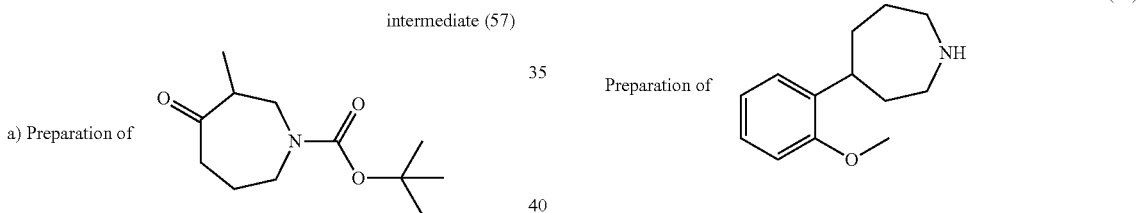

intermediate (57)

a) Preparation of

To a solution of intermediate (38) (5 g, 23 mmol) in THF (100 ml) was added N-(1-methylethyl)-2-propanamine lithium salt (23 ml, 46 mmol) at −78° C. The mixture was stirred for 0.5 hours at −50° C. Iodomethane (6.5 g, 46 mmol) was added to the mixture and stirred overnight at ambient temperature. The reaction mixture was quenched with 100 ml of brine. The organic layer was separated and the aqueous layer was extracted with EtOAc. The organic layers were combined and concentrated. The crude product was purified by column chromatography over silica gel (eluent: petroleum ether/EtOAc 9/1). The product fraction were collected and the solvent was evaporated, yielding 3 g of intermediate (57).

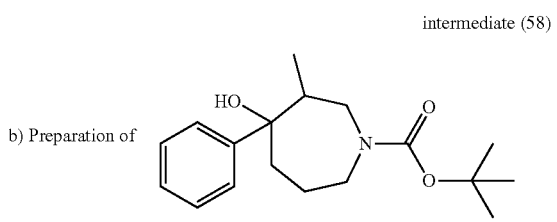 [SMILES: CC1CN(C(=O)OC(C)(C)C)CCCC1(O)c1ccccc1]

intermediate (58)

b) Preparation of

To a solution of intermediate (57) (1.7 g, 7.5 mmol) in THF (50 ml) was added bromophenyl-magnesium (3.7 ml, 11.2 mmol) at 0° C. The mixture was stirred overnight at ambient temperature. The reaction mixture was quenched with 50 ml of brine. The organic layer was separated and the aqueous layer was extracted with EtOAc. The organic layers were combined and concentrated. The crude product was purified by column chromatography over silica gel (eluent: petroleum ether/EtOAc 1/1). The product fraction were collected and the solvent was evaporated, yielding 0.5 g of intermediate (58).

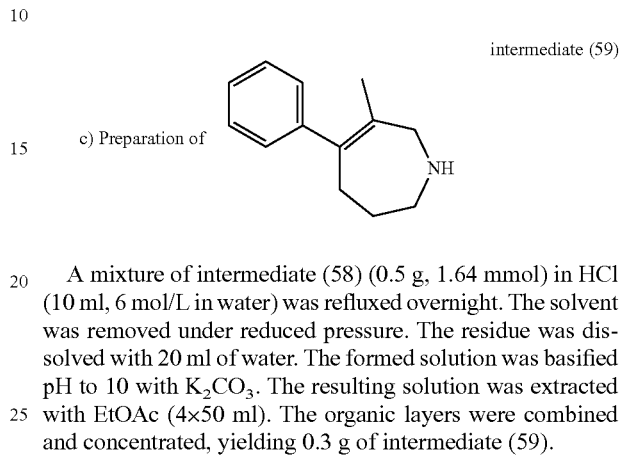

intermediate (59)

c) Preparation of

A mixture of intermediate (58) (0.5 g, 1.64 mmol) in HCl (10 ml, 6 mol/L in water) was refluxed overnight. The solvent was removed under reduced pressure. The residue was dissolved with 20 ml of water. The formed solution was basified pH to 10 with $K_2CO_3$. The resulting solution was extracted with EtOAc (4×50 ml). The organic layers were combined and concentrated, yielding 0.3 g of intermediate (59).

Example A.17

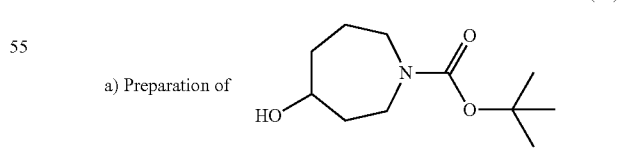

intermediate (60)

Preparation of

Intermediate (45) (4 mmol) in MeOH (40 mL) was hydrogenated at 40° C. (0.1 MPa) with $PtO_2$ (0.5 g) as a catalyst. After uptake of hydrogen (1 equivalent), the catalyst was filtered off and the filtrate was evaporated. The residue was purified by column chromatography over silica gel (eluent: DCM/MeOH 40/1). The product fractions were collected and the solvent was evaporated, yielding 1 g of intermediate (60).

Example A.18 intermediate (61)

a) Preparation of

Sodium borohydride (0.35 g, 9.38 mmol) was added slowly to a solution of intermediate (38) (2 g, 9.38 mmol) in MeOH (20 mL) under nitrogen flow at 0° C. The mixture was stirred 2 hours at room temperature. The mixture was poured out into water. The organic layer was extracted with EtOAc, washed with brine, dried over $MgSO_4$, filtered off and concentrated, yielding 1.62 g of intermediate (61).

b) Preparation of 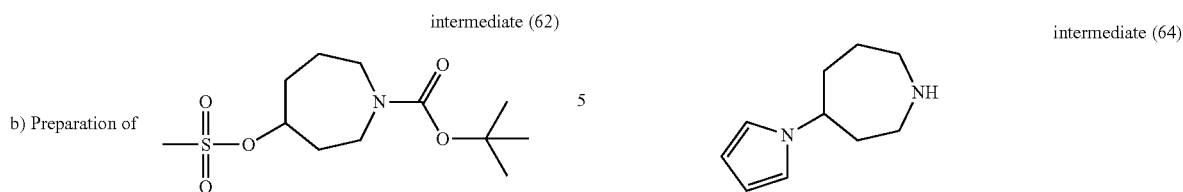

intermediate (62)

A solution of methanesulfonyl chloride (0.88 mL, 11.35 mmol) in DCM (10 mL) was added dropwise to a solution of intermediate (61) (1.88 g, 8.73 mmol) and triethylamine (3.64 mL, 26.2 mmol) in DCM (10 mL). The solution was stirred at room temperature for 2 hours. Water and DCM were added, and the organic layer was separated, dried over $MgSO_4$, filtered off and concentrated, yielding 2.53 g of intermediate (62). The product was used without further purification.

c) Preparation of 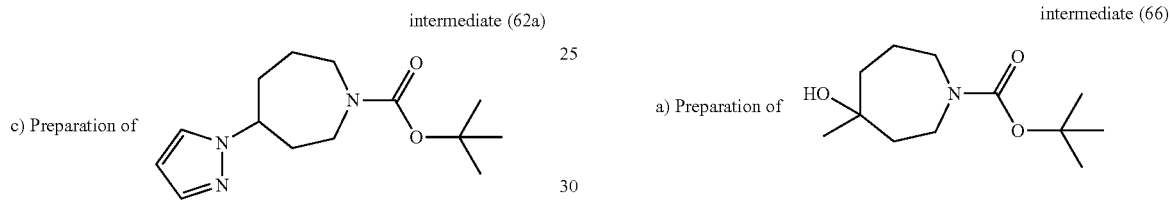

intermediate (62a)

Reaction under $N_2$. Sodium hydride (60% dispersion in mineral oil, 0.082 g, 2.05 mmol) was added portionwise at 5° C. to a solution of pyrazole (0.14 g, 2.05 mmol) in DMF (10 mL) and the mixture was stirred for 30 minutes. Intermediate (62) (0.506 g, 1.71 mmol) in DMF (5 mL) was added dropwise and the reaction mixture was allowed to reach room temperature and stirred overnight. Water and EtOAc were added. The organic layer was separated, washed with water then brine, dried ($MgSO_4$) and evaporated till dryness, yielding 446 mg of intermediate (62a). The residue was used as such for next step.

d) Preparation of 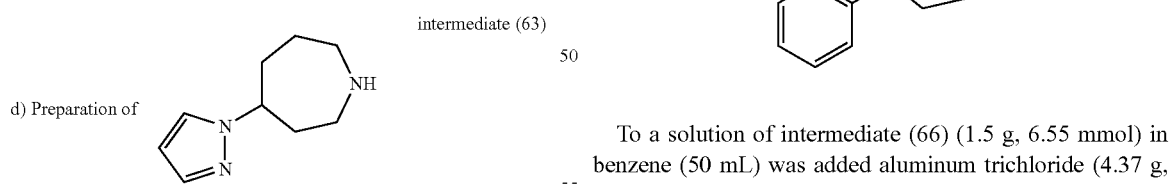

intermediate (63)

TFA (1.23 mL, 15.97 mmol) was added to a solution of intermediate (62a) (0.446 g, 1.6 mmol) in DCM (4 mL). The reaction mixture was stirred at room temperature for 3 hours, water and DCM were added, $K_2CO_3$ 10% was added to basify and the organic layer was separated, washed with water, dried ($MgSO_4$) and evaporated till dryness, yielding 78 mg of intermediate (63).

The following compounds were made using the same procedure as Example A.18 whereby 1H-pyrazole was replaced by 1H-pyrrole or 1H-[1,2,3]triazole respectively.

intermediate (64)

intermediate (65)

Example A.19 intermediate (66)

a) Preparation of

To a solution of intermediate (38) (3 g, 14.1 mmol) in THF (30 mL) was added bromomethyl-magnesium (5.64 mL, 16.92 mmol) at 0° C. The saturated $NH_4Cl$ aqueous solution (10 mL) was added. The formed mixture was extracted with DCM (2×20 mL). The combined organic layers were dried over $MgSO_4$, filtrated and the solvent was evaporated. The residue was purification by column chromatography over silica gel (eluent: DCM/MeOH 100/1). The desired fraction were collected and the solvent was evaporated, yielding 1.74 g of intermediate (66).

intermediate (67)

b) Preparation of

To a solution of intermediate (66) (1.5 g, 6.55 mmol) in benzene (50 mL) was added aluminum trichloride (4.37 g, 32.75 mmol). The formed mixture was refluxed over night. The reaction mixture was poured into ice, The formed solution was basified pH to 8, extracted with DCM (2×50 mL). The combined organic layers were dried over $MgSO_4$, filtrated and the solvent was evaporated. The residue was purification by column chromatography over silica gel (eluent: DCM/MeOH 10/1). The desired fraction were collected and the solvent was evaporated, yielding 520 mg of intermediate (67).

Some intermediate compounds used in the preparation of the final compounds are commercially available such as hexahydro-4-phenyl-1H-azepine, 2,3,4,5-tetrahydro-1H-3-benzazepine, hexahydro-1-phenyl-1H-1,4-diazepine, 4,4-difluorohexahydro-1H-azepine.

B. Synthesis of the Final Compounds

Example B.1 compound (1)

Preparation of

A mixture of intermediate (2) (0.192 g, 0.577 mmol), intermediate (7) (0.15 g, 0.866 mmol), EDCI (0.133 g, 0.693 mmol), HOBT (0.0936 g, 0.693 mmol) and triethylamine (0.193 ml, 1.39 mmol) in DCM (4 ml) and THF (4 ml) was stirred overnight at room temperature. Water and DCM were added, the organic layer was separated, washed with water, dried (MgSO$_4$) and evaporated till dryness. The residue was taken up in ethanol, filtered off and dried (vacuum), yielding compound (I).

Example B.2 compound (6)

Preparation of

A mixture of intermediate (40) (0.98 mmol), intermediate (2) (1 mmol), triethylamine (0.5 g) and HATU (0.4 g) in DMF (10 ml) was stirred at ambient temperature for one night. The solvent was evaporated. The residue was added DCM (20 ml) and washed with water (20 ml×2). The separated organic layer was dried (Na$_2$SO$_4$), filtered, and the solvent was evaporated. The residue was purified by column chromatography over silica gel (eluent: DCM/MeOH 5/1). The product fraction were collected and the solvent was evaporated, yielding 0.07 g of compound (6).

Example B.3

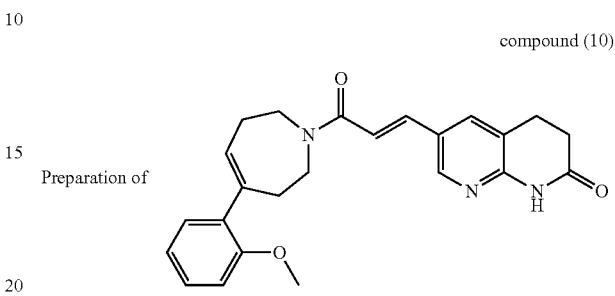

compound (10)

Preparation of

To a mixture of intermediate (45) (2.03 g, 10 mmol), intermediate (2) (3.3 g, 10 mmol) and HATU (3.80 g, 10 mmol) in DCM (100 mL) was added dropwise DIPEA (8 ml, 846 mmol) under nitrogen at 0° C. After the addition was complete, the resulting mixture was stirred overnight at room temperature. The reaction mixture was partitioned with water (300 mL) and EtOAc (300 mL), the water layer was extracted with EtOAc (4×200 mL). The combined organic layer were dried over Na$_2$SO$_4$, filtrated and the filtrate's solvent was evaporated. The residue was purified by column chromatography over silica gel (eluent: EtOAc). The products fraction were collected and the solvent was evaporated. The residue was crystallized from EtOAc, yielding 1.5 g of compound (10).

Example B.4

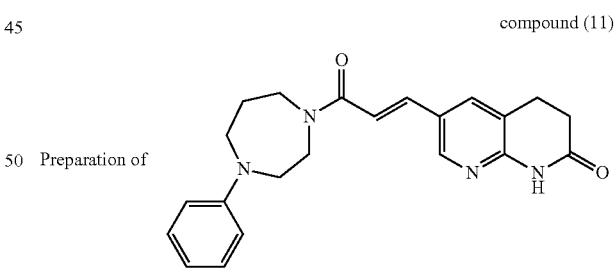

compound (11)

Preparation of

A solution of hexahydro-1-phenyl-1H-1,4-diazepine (0.085 g, 0.48 mmol), intermediate (2) (0.16 g, 0.48 mmol), 1-hydroxybenzotriazole (HOBT) (0.078 g, 0.58 mmol), 1-(3-dimethylaminopropyl)-3-ethylcarbodiimide hydrochloride (EDCI) (0.11 g, 0.58 mmol) and triethylamine (0.23 ml, 1.69 mmol) in DCM (4 ml) and THF (4 ml) was stirred overnight at room temperature. The mixture was poured out into water. The organic layer was extracted with DCM. The combined organic layers were washed with brine, dried over MgSO$_4$; filtered and concentrated. The residue was crystallized from acetonitrile, filtered off and dried under vacuum at 60° C. The residue was dried under vacuum at 70° C., yielding 0.079 g of compound (11) (mp=156° C.).

Example B.5

Preparation of 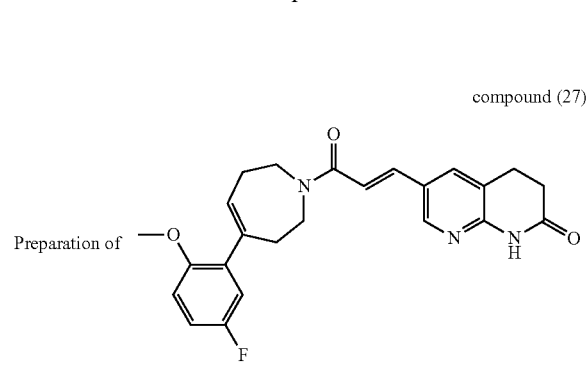 compound (27)

A mixture of intermediate (42) (1.5 g, 6.8 mmol), intermediate (2) (2.7 g, 8.14 mmol), triethylamine (2.2 g, 17 mmol) and EDCI (1.55 g, 8.14 mmol) in DCM (100 ml) was stirred at ambient temperature for one night. The solvent was evaporated. The residue was treated with DCM (100 ml) and the resulting mixture was washed with water (2×50 ml). The separated organic layer was dried ($Na_2SO_4$), filtered, and the solvent was evaporated. The residue was purified by column chromatography over silica gel (eluent: DCM/MeOH 20/1). The product fraction were collected and the solvent was evaporated, yielding 1 g of compound (27).

Example B.6

Preparation of 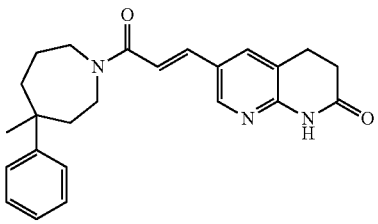 compound (28)

A mixture of intermediate (67) (0.13 g, 0.688 mmol), intermediate (2) (0.251 g, 0.757 mmol), EDCI (0.145 g, 0.757 mmol), HOBT (0.102 g, 0.757 mmol) and DIPEA (0.445 g, 3.44 mmol) in DCM (50 ml) was stirred at room temperature over night. The saturated $NH_4Cl$ aqueous solution (50 mL) was added. The formed mixture was extracted with DCM (2×20 mL). The combined organic layers were washed with saturated $NaHCO_3$ aqueous solution (30 mL) and brine (30 mL), dried over $MgSO_4$, filtrated and the filtrate's solvent was evaporated. The residue was purification by column chromatography over silica gel (eluent: DCM/MeOH 20/1) and preparative HPLC. The desired fraction were collected and the solvent was evaporated, yielding 55 mg of compound (28).

Table F-1 lists the compounds that were prepared according to one of the above Examples.

TABLE F-1

| | |
|---|---|
| 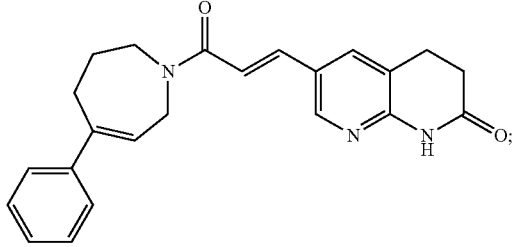 [SMILES: O=C1CCc2cc(/C=C/C(=O)N3CC=C(c4ccccc4)CCC3)cnc2N1]<br>Ex. B.1 | Co. No. 1 |
| 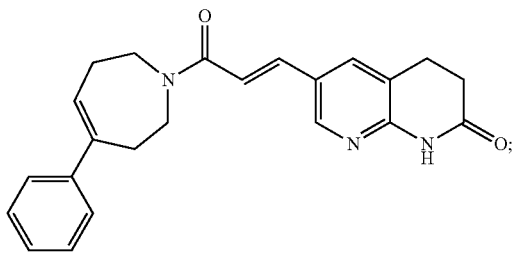 [SMILES: O=C1CCc2cc(/C=C/C(=O)N3CCC=C(c4ccccc4)CC3)cnc2N1]<br>Ex. B.1 | Co. No. 2 |
| 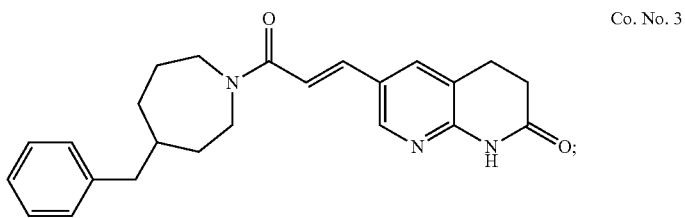<br>Ex. B.1 | Co. No. 3 |

TABLE F-1-continued
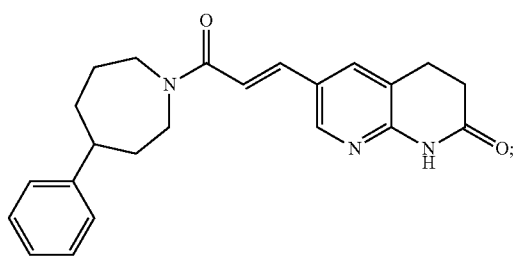
Co. No. 4
Ex. B.1
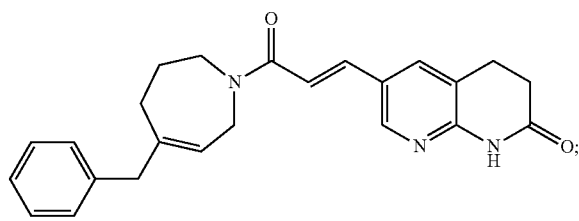 [SMILES: O=C1CCc2cc(/C=C/C(=O)N3CC=C(Cc4ccccc4)CCC3)cnc2N1]
Co. No. 5
Ex. B.1
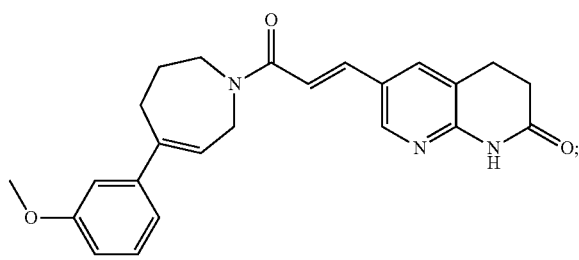 [SMILES: COc1cccc(C2=CCN(C(=O)/C=C/c3cnc4c(c3)CCC(=O)N4)CCC2)c1]
Co. No. 6
Ex. B.2
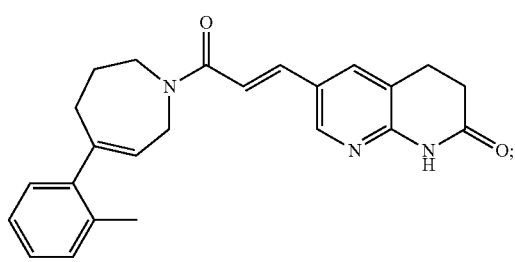 [SMILES: Cc1ccccc1C1=CCN(C(=O)/C=C/c2cnc3c(c2)CCC(=O)N3)CCC1]
Co. No. 7
Ex. B.2
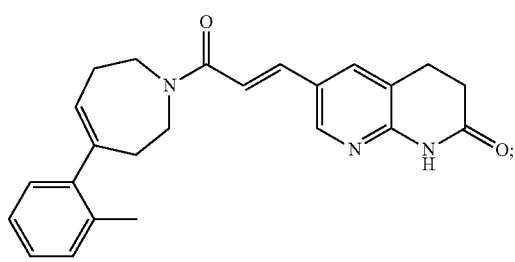 [SMILES: Cc1ccccc1C1=CCCN(C(=O)/C=C/c2cnc3c(c2)CCC(=O)N3)CC1]
Co. No. 8
Ex. B.2

TABLE F-1-continued
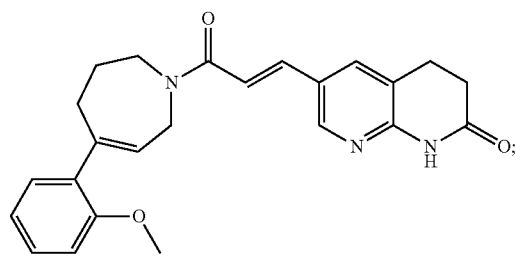
Co. No. 9
Ex. B.3
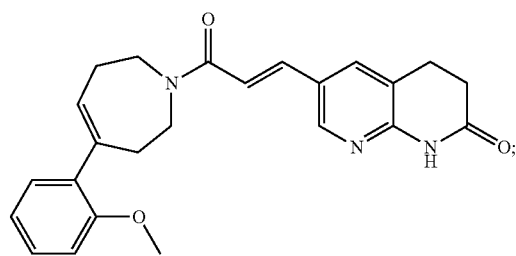 [SMILES: COc1ccccc1C1=CCCN(C(=O)/C=C/c2cnc3c(c2)CCC(=O)N3)CC1]
Co. No. 10
Ex. B.3
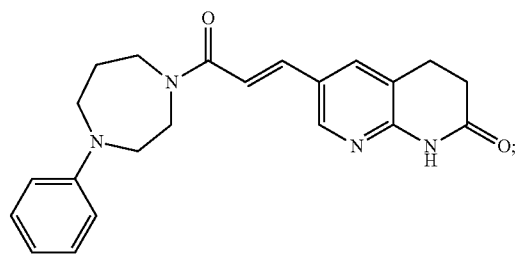 [SMILES: O=C1CCc2cc(/C=C/C(=O)N3CCCN(c4ccccc4)CC3)cnc2N1]
Co. No. 11
Ex. B.4
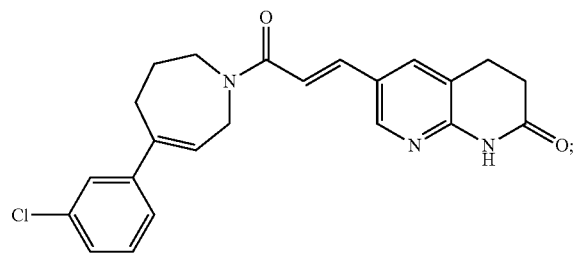 [SMILES: O=C1CCc2cc(/C=C/C(=O)N3CC=C(c4cccc(Cl)c4)CCC3)cnc2N1]
Co. No. 12
Ex. B.6
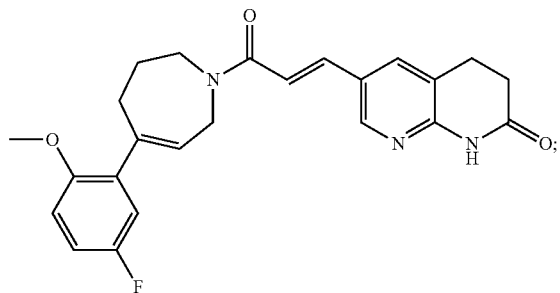 [SMILES: COc1ccc(F)cc1C1=CCN(C(=O)/C=C/c2cnc3c(c2)CCC(=O)N3)CCC1]
Co. No. 13
Ex. B.2

TABLE F-1-continued
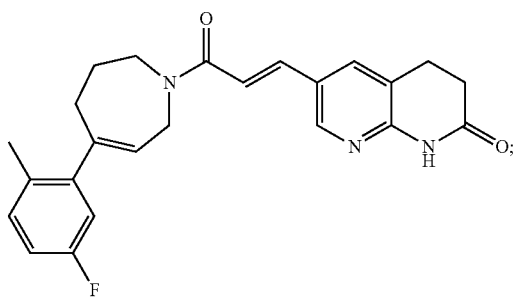 [SMILES: Cc1ccc(F)cc1C1=CCN(C(=O)/C=C/c2cnc3c(c2)CCC(=O)N3)CCC1]
Co. No. 14
Ex. B.3
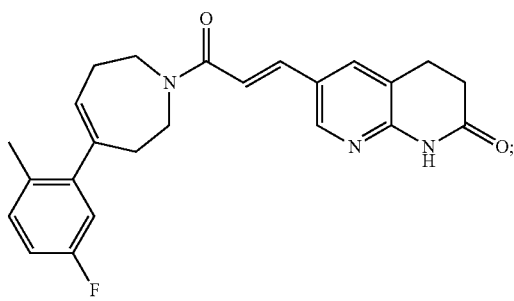 [SMILES: Cc1ccc(F)cc1C1=CCCN(C(=O)/C=C/c2cnc3c(c2)CCC(=O)N3)CC1]
Co. No. 15
Ex. B.3
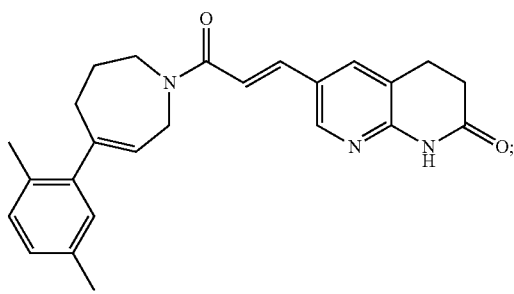 [SMILES: Cc1ccc(C)c(C2=CCN(C(=O)/C=C/c3cnc4c(c3)CCC(=O)N4)CCC2)c1]
Co. No. 16
Ex. B.2
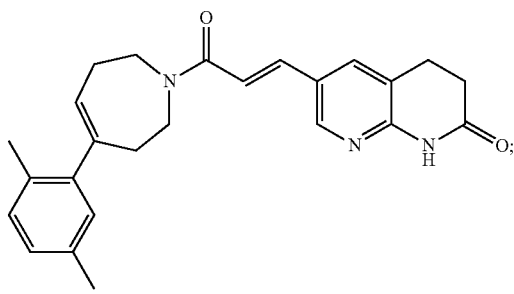 [SMILES: Cc1ccc(C)c(C2=CCCN(C(=O)/C=C/c3cnc4c(c3)CCC(=O)N4)CC2)c1]
Co. No. 17
Ex. B.2

TABLE F-1-continued
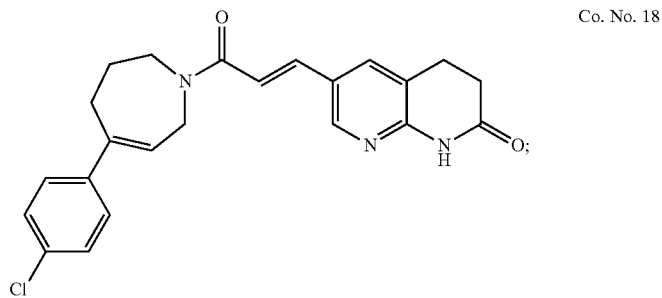
Co. No. 18
Ex. B.2
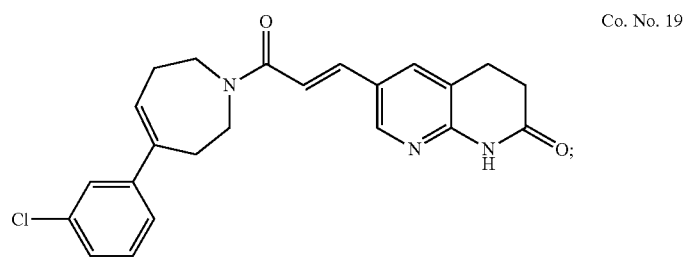
Co. No. 19
Ex. B.1
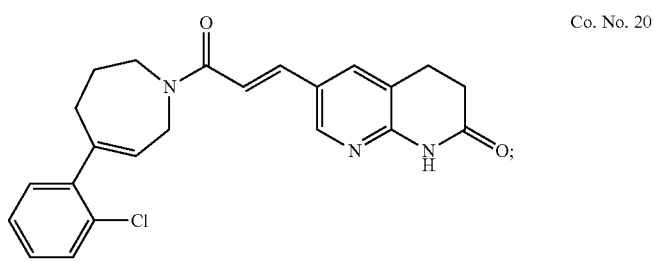
Co. No. 20
Ex. B.6
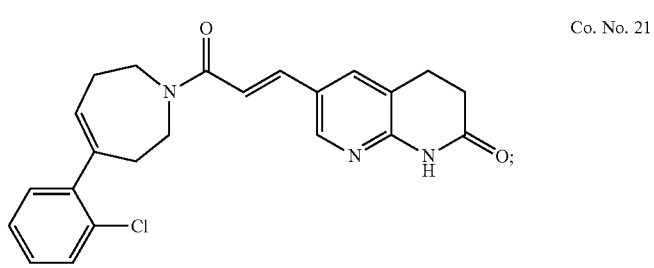
Co. No. 21
Ex. B.6
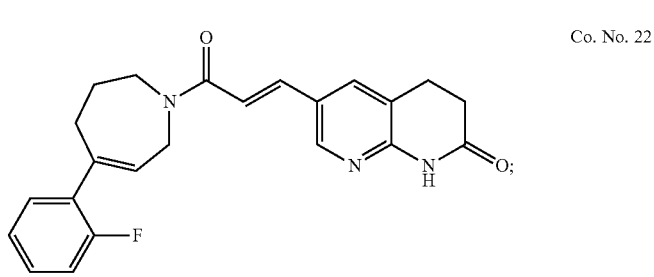
Co. No. 22
Ex. B.2

TABLE F-1-continued
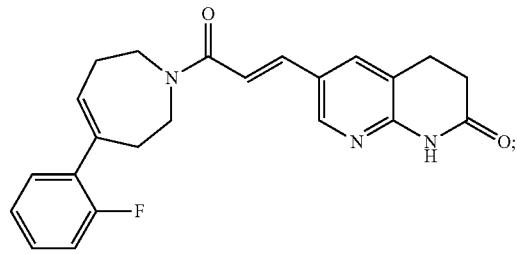
Co. No. 23
Ex. B.2
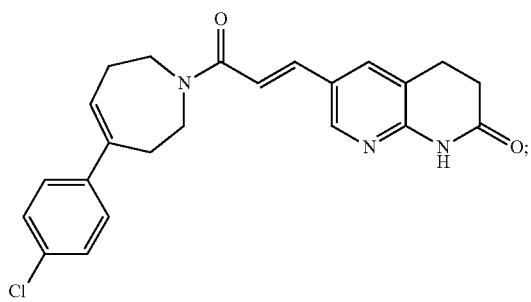 [SMILES: O=C1CCc2cc(/C=C/C(=O)N3CCC=C(c4ccc(Cl)cc4)CC3)cnc2N1]
Co. No. 24
Ex. B.2
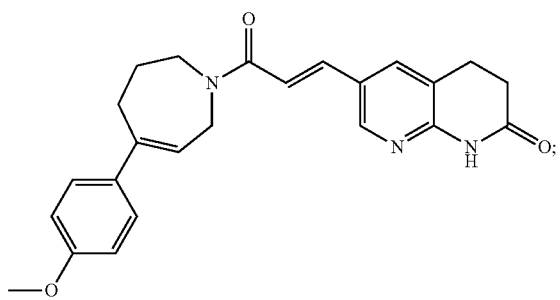 [SMILES: COc1ccc(C2=CCN(C(=O)/C=C/c3cnc4c(c3)CCC(=O)N4)CCC2)cc1]
Co. No. 25
Ex. B.3
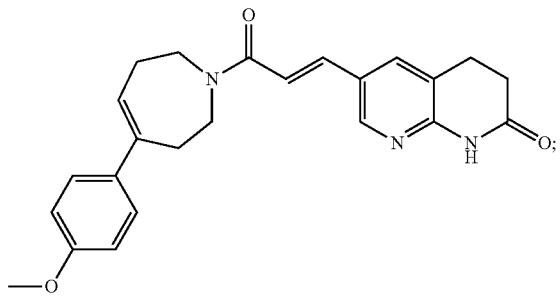 [SMILES: COc1ccc(C2=CCCN(C(=O)/C=C/c3cnc4c(c3)CCC(=O)N4)CC2)cc1]
Co. No. 26
Ex. B.3

TABLE F-1-continued
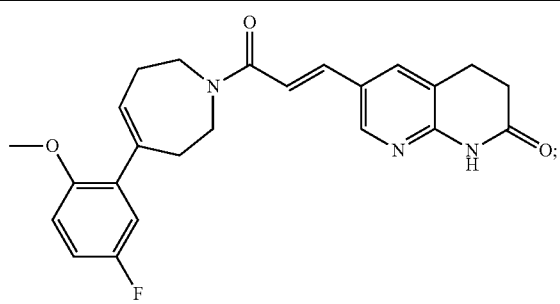
Co. No. 27
Ex. B.5
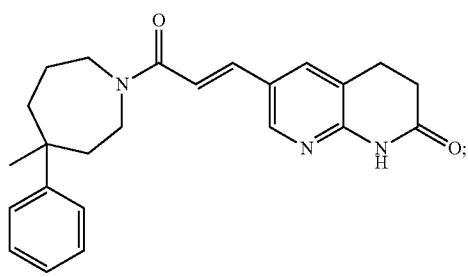 [SMILES: CC1(c2ccccc2)CCCN(C(=O)/C=C/c2cnc3c(c2)CCC(=O)N3)CC1]
Co. No. 28
Ex. B.6
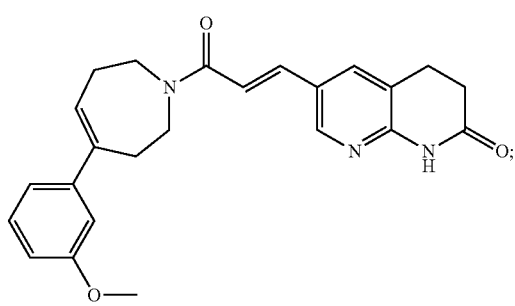 [SMILES: COc1cccc(C2=CCCN(C(=O)/C=C/c3cnc4c(c3)CCC(=O)N4)CC2)c1]
Co. No. 29
Ex. B.3
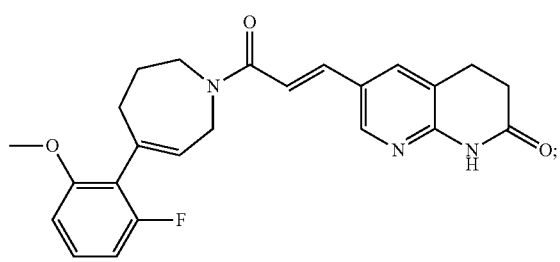 [SMILES: COc1cccc(F)c1C1=CCN(C(=O)/C=C/c2cnc3c(c2)CCC(=O)N3)CCC1]
Co. No. 30
Ex. B.2
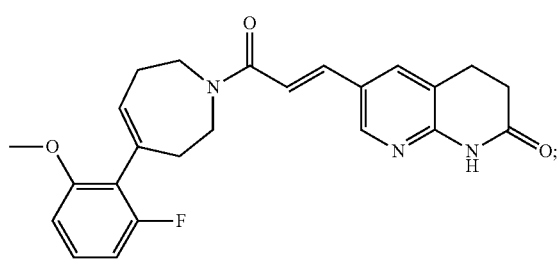 [SMILES: COc1cccc(F)c1C1=CCCN(C(=O)/C=C/c2cnc3c(c2)CCC(=O)N3)CC1]
Co. No. 31
Ex. B.2

TABLE F-1-continued
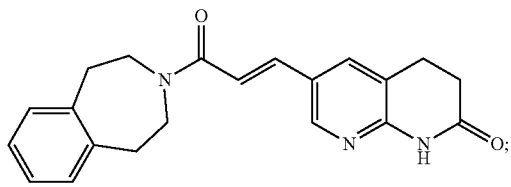 [SMILES: O=C1CCc2cc(/C=C/C(=O)N3CCc4ccccc4CC3)cnc2N1]
Co. No. 32
Ex. B.1
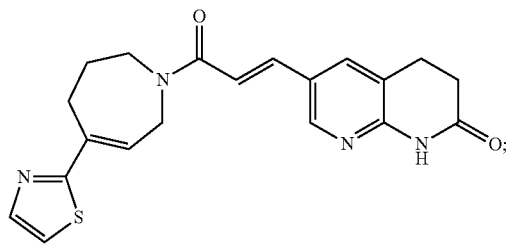 [SMILES: O=C1CCc2cc(/C=C/C(=O)N3CC=C(c4nccs4)CCC3)cnc2N1]
Co. No. 33
Ex. B.1
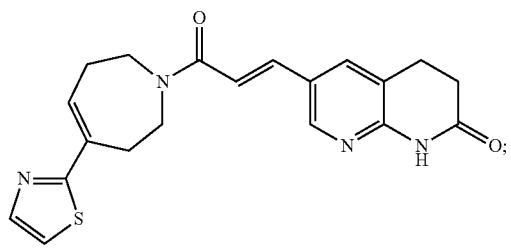 [SMILES: O=C1CCc2cc(/C=C/C(=O)N3CCC=C(c4nccs4)CC3)cnc2N1]
Co. No. 34
Ex. B.1
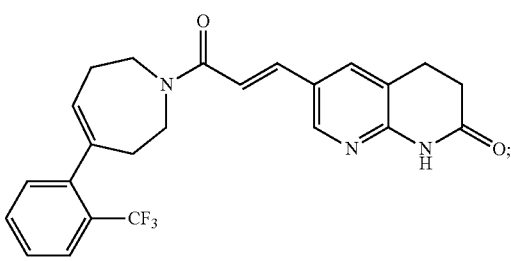
Co. No. 35
Ex. B.1
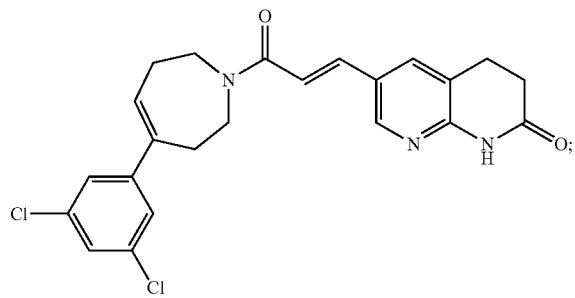 [SMILES: O=C1CCc2cc(/C=C/C(=O)N3CCC=C(c4cc(Cl)cc(Cl)c4)CC3)cnc2N1]
Co. No. 36
Ex. B.1

TABLE F-1-continued
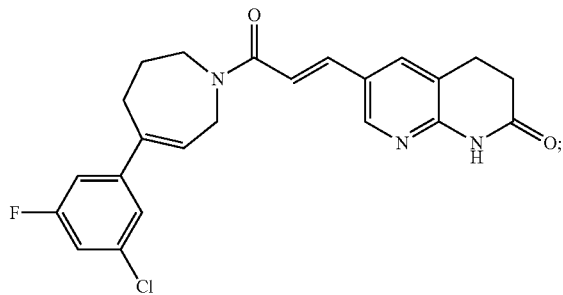 [SMILES: O=C1CCc2cc(/C=C/C(=O)N3CC=C(c4cc(F)cc(Cl)c4)CCC3)cnc2N1]
Co. No. 37
Ex. B.1
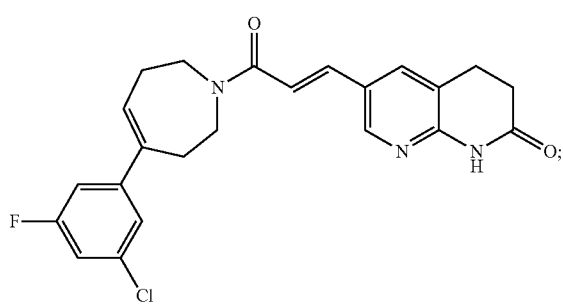 [SMILES: O=C1CCc2cc(/C=C/C(=O)N3CCC=C(c4cc(F)cc(Cl)c4)CC3)cnc2N1]
Co. No. 38
Ex. B.1
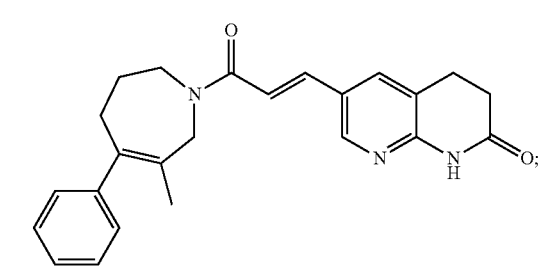 [SMILES: CC1=C(c2ccccc2)CCCN(C(=O)/C=C/c2cnc3c(c2)CCC(=O)N3)C1]
Co. No. 39
Ex. B.5
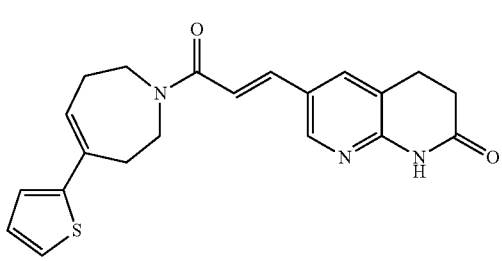 [SMILES: O=C1CCc2cc(/C=C/C(=O)N3CCC=C(c4cccs4)CC3)cnc2N1]
Co. No. 40
Ex. B.1
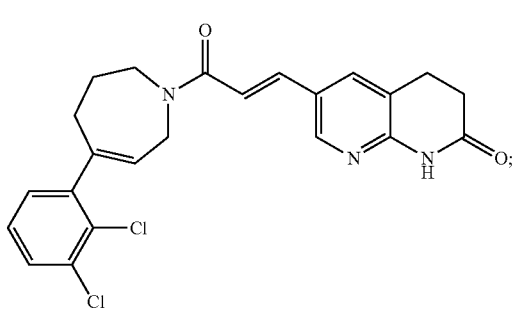 [SMILES: O=C1CCc2cc(/C=C/C(=O)N3CC=C(c4cccc(Cl)c4Cl)CCC3)cnc2N1]
Co. No. 41
Ex. B.1

TABLE F-1-continued
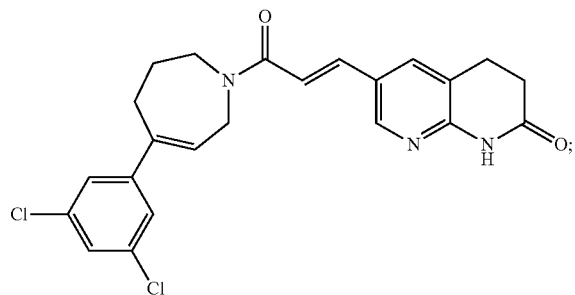 [SMILES: O=C1CCc2cc(/C=C/C(=O)N3CC=C(c4cc(Cl)cc(Cl)c4)CCC3)cnc2N1]
Co. No. 42
Ex. B.1
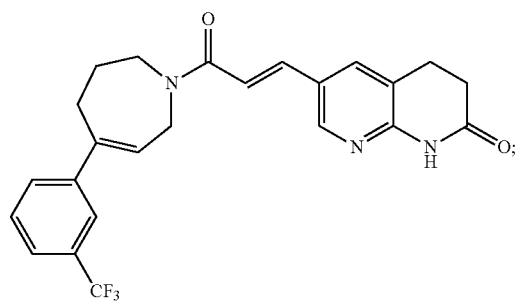 [SMILES: O=C1CCc2cc(/C=C/C(=O)N3CC=C(c4cccc(C(F)(F)F)c4)CCC3)cnc2N1]
Co. No. 43
Ex. B.1
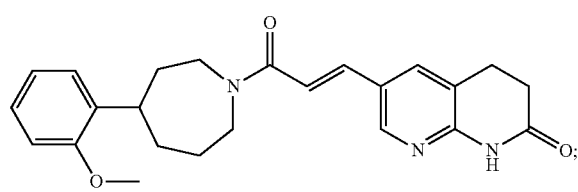 [SMILES: COc1ccccc1C1CCCN(C(=O)/C=C/c2cnc3c(c2)CCC(=O)N3)CC1]
Co. No. 44
Ex. B.5
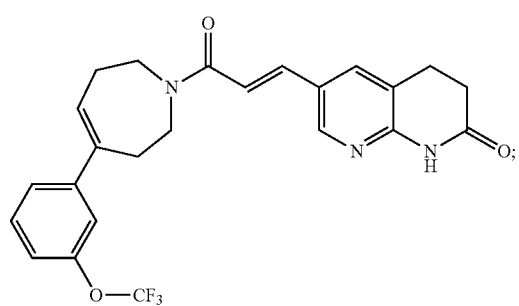 [SMILES: O=C1CCc2cc(/C=C/C(=O)N3CCC=C(c4cccc(OC(F)(F)F)c4)CC3)cnc2N1]
Co. No. 45
Ex. B.1
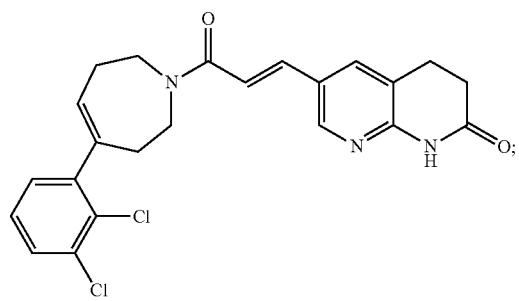 [SMILES: O=C1CCc2cc(/C=C/C(=O)N3CCC=C(c4cccc(Cl)c4Cl)CC3)cnc2N1]
Co. No. 46
Ex. B.1

TABLE F-1-continued
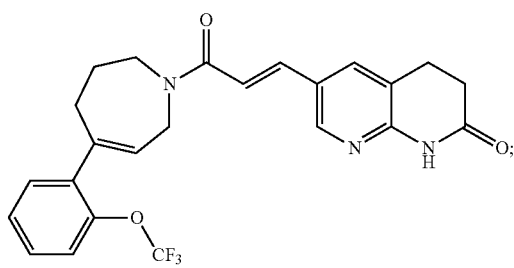
Co. No. 47
Ex. B.1
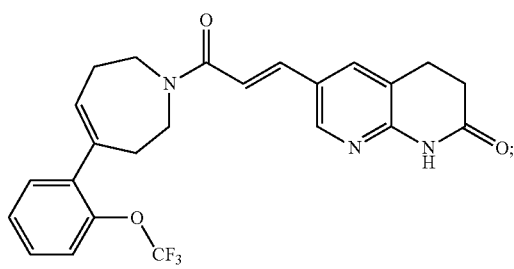 [SMILES: O=C1CCc2cc(/C=C/C(=O)N3CCC=C(c4ccccc4OC(F)(F)F)CC3)cnc2N1]
Co. No. 48
Ex. B.1
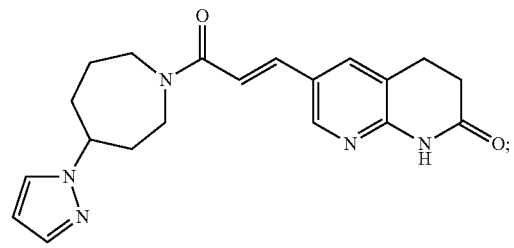 [SMILES: O=C1CCc2cc(/C=C/C(=O)N3CCCC(n4cccn4)CC3)cnc2N1]
Co. No. 49
Ex. B.4
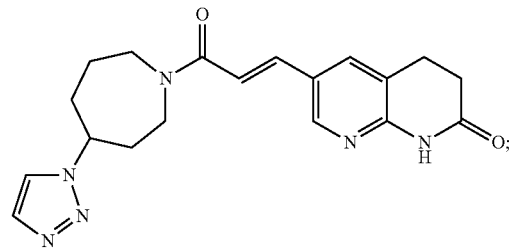 [SMILES: O=C1CCc2cc(/C=C/C(=O)N3CCCC(n4ccnn4)CC3)cnc2N1]
Co. No. 50
Ex. B.4
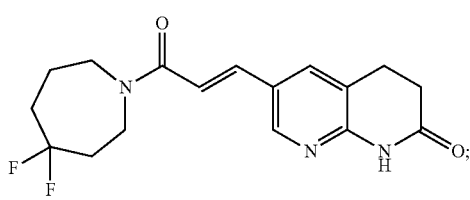 [SMILES: O=C1CCc2cc(/C=C/C(=O)N3CCCC(F)(F)CC3)cnc2N1]
Co. No. 51
Ex. B.4

TABLE F-1-continued

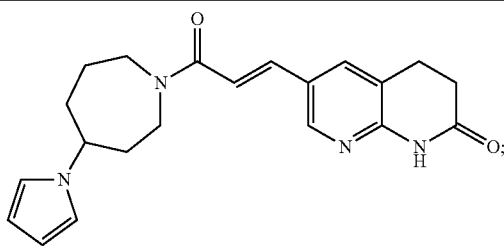

Co. No. 52

Ex. B.4

C. Compound Identification

C1. LCMS

For LCMS-characterization of the compounds of the present invention, the following methods were used.
General Procedure A
The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.
Method 1
In addition to the general procedure A: reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.
Method 2
In addition to the general procedure A: reversed phase UPLC was carried out on a Waters Acquity BEH (bridged ethylsiloxane/silica hybrid) C18 column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 μl was used. Cone voltage was 20V for positive and negative ionization mode. Mass spectra were acquired by scanning from 100 to 1000 in 0.2 seconds using an interscan delay of 0.1 seconds.
Method 3
In addition to the general procedure A: reversed phase UPLC was carried out on a Halo C18 column (2.7 μm, 4.6×50 mm) with a flow rate of 1.8 ml/min. Two mobile phases (mobile phase A: H$_2$O (0.05% FA); mobile phase B: acetonitrile (0.05% FA) were employed to run a gradient condition from 95% A and 5% B to 5% A and 95% B from time zero to 1 minute, then hold for 1 minute, then back to 95% A in 1 minute and hold for 0.5 minutes. An injection volume of 2 μl was used. Cone voltage was 20V for positive and negative ionization mode. Mass spectra were acquired by scanning from 100 to 1000 in 0.2 seconds using an interscan delay of 0.1 seconds.

TABLE C.1

| | LC/MS data | | |
|---|---|---|---|
| Co. No. | Rt (min) | MH$^+$ | LC/MS Method |
| 5 | 1.42 | 386.1 | 3 |
| 30 | 3.14 | 378 | 1 |
| 43 | 2.95 | 458 | 2 |
| 49 | 1.91 | 366 | 2 |
| 50 | 1.93 | 367 | 2 |

C2. Melting Points

For a number of compounds, melting points were obtained with a Kofler hot bench, consisting of a heated plate with linear temperature gradient, a sliding pointer and a temperature scale in degrees Celsius.

For a number of compounds, melting points were determined using differential scanning calorimetry (DSC). Melting points were measured with a temperature gradient of 10° C./minute. Maximum temperature was 400° C.

The remaining melting points were determined using open capillary tubes.

TABLE C.2

| | melting point data | |
|---|---|---|
| Co. No. | Melting point | Method |
| 1 | 204.19° C. | DSC |
| 2 | 198.48° C. | DSC |
| 3 | 158.02° C. | DSC |
| 4 | 241.93° C. | DSC |
| 6 | 176° C. | Kofler |
| 7 | 118.3-118.6° C. | — |
| 8 | 98-99° C. | — |
| 9 | 81.5-82.9° C. | — |
| 10 | 192.2-193.1° C. | — |
| 11 | 229.62° C. | DSC |
| 12 | 205.26° C. | DSC |
| 13 | 184.5-185° C. | — |
| 14 | 95-97° C. | — |
| 15 | 185° C. | Kofler |

TABLE C.2-continued melting point data

| Co. No. | Melting point | Method |
|---|---|---|
| 16 | 99.6-100.7° C. | — |
| 17 | 93.5-94° C. | — |
| 18 | 165° C. | Kofler |
| 19 | 201.20° C. | DSC |
| 20 | 238.68° C. | DSC |
| 21 | >240° C. | Kofler |
| 22 | 113.5-114° C. | — |
| 23 | 196-197° C. | — |
| 24 | 267.45° C. | DSC |
| 25 | 165° C. | Kofler |
| 26 | 222-223° C. | — |
| 27 | 102.5-103° C. | — |
| 28 | 231-232.5° C. | — |
| 29 | 165° C. | Kofler |
| 31 | 78.5-80.4° C. | — |
| 32 | 272.27° C. | DSC |
| 33 | 75.2-76.9° C. | — |
| 34 | 228° C. | Kofler |
| 35 | 136° C. | Kofler |
| 36 | 66.5-68.5° C. | — |
| 37 | 199.50° | DSC |
| 38 | 204° C. | Kofler |
| 39 | 82.5-83.5° C. | — |
| 40 | 209.35° | DSC |
| 41 | 161° C. | Kofler |
| 42 | 94-95° C. | — |
| 44 | >250° C. | Kofler |
| 45 | >250° C. | Kofler |
| 46 | 132° C. | Kofler |
| 47 | 108° C. | Kofler |
| 48 | 174.63° | DSC |
| 51 | 164° C. | Kofler |
| 52 | 182° C. | Kofler |

D. Pharmacological Examples

D.1 FabI Enzyme Inhibition: *Staphylococcus aureus* FabI Enzyme Inhibition Assay FabI enzyme inhibition assays were carried out in half-area, 384-well microtitre plates. Compounds were evaluated in 40-μl assay mixtures containing 100 mM NaADA, pH 6.5 (ADA=N-[2-acetamido]-2iminodiacetic acid), 250 μM crotonoyl-CoA, 625 μM NADH and 50 μg/ml *S. aureus* ATCC 29213 FabI Inhibitors were typically varied over the range of 50 to 0.39 μM. The reaction mixtures were incubated for 30 minutes at room temperature and the reaction was stopped by adding 200 mM Tris buffer (pH 9.0) to create a pH-shift. The consumption of NADH was monitored by measuring the change in absorbance at 340. By comparing sample readings to those of negative (absence of compound) and positive (absence of enzyme) controls, the percent inhibition of enzymatic activity of the compounds was determined. A best-fit curve is fitted by a minimum of squares method. From this an $IC_{50}$-value (expressed in μg/ml), resulting in 50% inhibition of enzymatic activity, was obtained.

TABLE D.1

*S. aureus* FabI $IC_{50}$ values

| Co. No. | FabI $IC_{50}$ μg/mL |
|---|---|
| 1 | 0.36 |
| 2 | 0.33 |
| 3 | 0.38 |
| 4 | 0.25 |
| 5 | 0.2 |
| 5 | 0.37 |
| 7 | 0.44 |
| 8 | 0.33 |
| 9 | 0.39 |
| 10 | 0.35 |
| 11 | 0.39 |
| 12 | 0.51 |
| 13 | 0.58 |
| 14 | 0.35 |
| 15 | 0.32 |
| 16 | 0.38 |
| 17 | 0.38 |
| 18 | 0.58 |
| 19 | 0.43 |
| 20 | 0.32 |
| 21 | 0.38 |
| 22 | 0.26 |
| 23 | 0.42 |
| 24 | 0.78 |
| 25 | 0.86 |
| 26 | 0.67 |
| 27 | 0.45 |
| 28 | ~0.65 |
| 29 | 0.97 |
| 31 | 0.68 |
| 32 | 0.53 |
| 33 | 0.41 |
| 34 | 0.39 |
| 35 | 0.62 |
| 36 | 1.09 |
| 37 | 0.72 |
| 38 | 0.66 |
| 39 | 1.07 |
| 40 | 0.4 |
| 41 | 0.84 |
| 42 | 1.01 |
| 43 | 0.67 |
| 44 | 0.48 |
| 45 | 0.76 |
| 46 | 0.82 |
| 47 | 0.68 |
| 48 | 0.68 |
| 49 | 1.67 |
| 50 | 0.80 |
| 51 | 4.22 |
| 52 | 1.70 |

D.2 In Vitro Method for Testing Compounds for Antibacterial Activity Against Various Bacterial Strains Preparation of Bacterial Suspensions for Susceptibility Testing The following bacteria were used: *Staphylococcus aureus* ATCC 29213, methicillin-resistant *Staphylococcus aureus* (MRSA) ATCC 700788 and *Escherichia coli* ATCC 35218. The bacteria used in this study were grown overnight in flasks containing 100 ml Mueller-Hinton broth (Difco cat. nr. 0757-17) in sterile de-ionized water, with shaking, at 37° C. Stocks were store at −70° C. until use.

Bacteria were incubated on a tryptic soy agar plate containing 5% sheep blood (Becton Dickinson cat. nr. 254053) for 18-24 hours at 35° C. in aerobic conditions (first passage). For the second passage, fresh Mueller-Hinton broth is inoculated with 5-10 colonies and grown overnight at 35° C. until turbidity (reaching log-phase) in aerobic conditions is reached. The bacterial suspension is then adjusted to 0.5 McFarland density and further diluted 1:100 in Mueller Hinton broth medium. This is used as inoculum.

The results (for STA ATCC 29213) are depicted in the table D2 below.

Antibacterial Susceptibility Testing: $IC_{90}$ Determination

MIC assays were performed by the broth microdilution method in a 96-well format (flat-bottom microtitre plates) with a final volume of 0.1 ml Mueller Hinton broth containing two-fold serial dilutions of compounds and inoculated with $5 \times 10^5$ CFU/ml of bacteria (standard inoculum size according to CLSI guidelines). Inhibitors are typically varied over the range of 63 to 0.49 μM. The final DMSO concentration in the assay was 1.25% (maximum tolerable DMSO concentration=6%). In the assays where the effect of human serum on the activity of the compounds against *S. aureus* was tested, human serum was added at a final concentration of 10%. The plates were incubated at 35° C. for 16-20 hours. At the end of incubation the bacterial growth was quantified fluorometrically. For this, resazurin was added to all wells and the plates were re-incubated. The incubation time is dependent on the type of bacteria. A change in color from blue to pink indicated the growth of bacteria. The fluorescence was read in computer-controlled fluorometer (Fluoroskan Ascent FL, Labsystems) at an excitation wavelength 540 nm and an emission wavelength of 590 nm. The % growth inhibition achieved by the compounds was calculated according to standard methods. The $IC_{90}$ (expressed in μg/ml) was defined as the 90% inhibitory concentration for bacterial growth. A panel of reference compounds were simultaneously tested for QC approval.

The results are depicted in the table D2 below (STA+10% HS).

Cytotoxicity Assays

Cytotoxicity of the compounds was evaluated using the MTT assay. Human HelaM cells grown in 96-well plates were exposed to serial dilutions of the tested compounds (final volume of 0.2 ml) and incubated for 72 hours at 37° C. and 5% $CO_2$. Inhibitors are typically varied over the range of 25 to 0.8 μM. The final DMSO concentration in the assay is 0.5%. MTT (3-(4,5-Dimethylthiazol-2-yl)-2,5-diphenyltetrazolium bromide, a tetrazole) was added and reduced to purple formazan only in living cells. Solubilization of the formazan crystals was achieved by adding 100 μl 2-propanol. Cell viability was determined by measuring the absorbance of the reduced formazan, giving a purple color, at 540 nm and 690 nm. The absorbance measured at 690 nm was automatically subtracted from the absorbance at 540 nm, to eliminate the effects of non-specific absorption. The percent cytotoxicity achieved by the compounds was calculated according to standard methods. Cytotoxicity is reported as $CC_{50}$, the concentration that causes a 50% reduction in cell viability.

The results are depicted in the table D2 below (TOX HELAM).

TABLE D2 data for representative examples

| Cpd. No. | STA (361.159) IC90 μg/mL | STA + 10% HS (361.169) IC90 μg/mL | TOX HELAM (222.125) CC50 μg/mL |
|---|---|---|---|
| 2 | 0.14 | 0.33 | >9.38089 |
| 3 | 3.94 | 11.23 | >9.7838 |
| 4 | 3.42 | 3.54 | >9.43138 |
| 5 | 4.66 | 10.92 | >9.73331 |
| 6 | 3.21 | 6.32 | >10.1352 |
| 7 | 1.47 | 2.97 | >9.73331 |
| 8 | 0.69 | 0.84 | 9.30 |
| 9 | 0.99 | 1.48 | >10.1352 |
| 10 | 0.09 | 0.20 | >10.1352 |

TABLE D2-continued data for representative examples

| Cpd. No. | STA (361.159) IC90 μg/mL | STA + 10% HS (361.169) IC90 μg/mL | TOX HELAM (222.125) CC50 μg/mL |
|---|---|---|---|
| 11 | 3.24 | 5.76 | >9.45625 |
| 12 | 0.71 | 4.37 | 8.23 |
| 13 | 1.43 | 3.05 | >10.5871 |
| 14 | 1.54 | 3.74 | 9.73 |
| 15 | 0.39 | 1.02 | 8.57 |
| 16 | 1.49 | 3.01 | 9.09 |
| 17 | 0.33 | 0.72 | 4.11 |
| 18 | 1.52 | 5.08 | 6.85 |
| 19 | 0.35 | 1.38 | >20.4434 |
| 20 | 0.63 | 1.15 | 8.52 |
| 21 | <0.199781 | 0.36 | 9.24 |
| 22 | 0.59 | 1.03 | 12.52 |
| 23 | 0.18 | 0.35 | >9.83278 |
| 24 | 1.52 | 6.17 | 7.25 |
| 25 | 3.06 | 5.83 | >10.1352 |
| 26 | 1.46 | 2.86 | >10.1352 |
| 27 | 0.10 | 0.33 | >10.5871 |
| 28 | 2.40 | 7.42 | >9.7838 |
| 29 | 0.78 | 1.66 | >10.5871 |
| 31 | 0.21 | 0.26 | >10.5871 |
| 32 | 21.42 | 20.22 | >8.7268 |

Example E

E.1 Thermodynamic Solubility/Solubility in Aqueous Solution

The pH solubility profiling was carried out at ambient temperature for a period of 4 days. A saturation solubility study was carried out in order to determine maximum solubility in a particular buffer solution. The compound was added to respective buffer solution until saturation point is reached. This was followed by shaking the flask for 4 days at ambient temperature. After 4 days, the solutions were filtered and injected on UPLC and the concentration was determined using a generic HPLC method.

Results

| | Co. No. 27 | Co. No. 2 |
|---|---|---|
| Buffer pH 2 | <0.01 | 0.002 |
| 10% HP-β-CD buffer pH 2 | NT | NT |
| 20% HP-β-CD buffer pH 2 | NT | NT |
| Buffer pH 4 | <0.01 | <0.002 |
| 10% HP-β-CD buffer pH 4 | 0.22 | 1.150 |
| 20% HP-β-CD buffer pH 4 | 0.44 | 0.980 |
| Buffer pH 7.4 | <0.01 | 0.003 |
| 10% HP-β-CD buffer pH 7.4 | 0.25 | 1.082 |
| 20% HP-β-CD buffer pH 7.4 | 0.59 | 1.054 |

NT = not tested

E.2 Antimicrobial Spectrum of Activity

Minimum Inhibitory Concentrations (MICs) were determined in accordance with the Clinical and Laboratory Standards Institute (CLSI) methodology against aerobic bacteria (CLSI M07-A8) (see Clinical and Laboratory Standards Institute. 2009. Methods for dilution antimicrobial susceptibility tests for bacteria that grow aerobically. CLSI document M07-A8, Vol. 29, No. 2.) by the broth microdilution method with cation-adjusted Mueller-Hinton broth (CA-MHB) medium for the majority of organisms, except for *Haemophilus influenza*, where Haemophilis test medium (HTM) broth was used. Descriptions of the individual organisms can be found in the table. Where possible, ATCC standard strains were tested.

The inoculum density for the susceptibility testing was standardized to give a final inoculum of approximately $5 \times 10^5$ CFU/mL. The broth MIC was determined as the lowest concentration of drug that prevented visible growth after 16-24 hours (species dependent) of incubation at 35° C.-37° C.

TABLE

Description of individual organisms tested

| Organism | Characteristics | MIC test medium |
|---|---|---|
| Staphylococcus aureus | ATCC 29213; reference strain MSSA | MHB |
| Staphylococcus aureus | ATCC 43300; reference strain MRSA | MHB |
| Staphylococcus aureus | NRS119; LZD-R; SCCmec IV; origin: US | MHB |
| Staphylococcus aureus | NRS120; LZD-R; SCCmec IV; origin: US | MHB |
| Staphylococcus aureus | NRS121; LZD-R; SCCmec IV; origin: US | MHB |
| Escherichia coli | ATCC 25922; reference strain | MHB |
| Escherichia coli | Tol C mutant | MHB |
| Haemophilus influenzae | ATCC 49247; reference strain | HTM broth |
| Moraxella catarrhalis | ATCC 8176; b-lactamase negative | MHB |

Stock solutions of the compounds were prepared in DMSO at concentrations of 1 mg/mL. Linezolid was prepared in DMSO at a concentration of 2 mg/mL. Stock solutions of all compounds were diluted into CA-MHB to give a range of two-fold dilutions, depending upon the sensitivity of the organism being tested.

Results (where Available)

| | Compound Nos. and $MIC_{90}$ (µg/ml) | | | |
|---|---|---|---|---|
| Organism | 27 | 19 | 2 | 10 |
| S. aureus ATCC 29213 | 0.06 | 0.125 | 0.06 | |
| S. aureus ATCC 43300 | 0.06 | 0.25 | 0.06 | |
| S. aureus NRS119 | 0.06 | | 0.125 | |
| S. aureus NRS120 | 0.125 | | 0.06 | |
| S. aureus NRS121 | 0.06 | | 0.125 | |
| E. coli tolC mutant | >8 | 1 | 0.25 | |
| E. coli ATCC 25922 | >8 | >8 | >32 | |
| H. influenza ATCC 49247 | >8 | >8 | | |
| M. catarrhalis ATCC 8176 | 1 | | | |

E.3 In Vivo Pharmacokinetic and Oral Bioavailability

The in vivo pharmacokinetics and oral bioavailability of the compound of the examples was/is investigated in male Swiss mice (fed) following single intravenous (i.v.) bolus and oral (p.o.) administration. For the i.v. and p.o. solution formulations, the compound was/is dissolved in a 20% HP-β-CD solution. The pH of the formulations was/is around pH 4. All i.v. formulations were isotonic.

Results

| | Co. No. 10 | Co. No. 14 | Co. No. 27 |
|---|---|---|---|
| | i.v. | | |
| Dose (mg/kg) | 2.5 | 2.5 | 2.5 |
| n | 3 | 3 | 3 |
| $C_0$ (ng/mL) | 3402 | 4550 | 3350 |
| Plasma clearance Cl (L/h/kg) | 1.2 | 0.36 | 0.75 |
| $Vd_z$ (L/kg) | 2.0 | 1.0 | 1.2 |
| $AUC_{0-inf}$ (ng·h/mL) | 2165 | 6699 | 3562 |
| Half life ($t_{1/2}$) (h) | 1.2 | 2.0 | 1.1 |
| | p.o. | | |
| Dose (mg/kg) | 10 | 10 | 10 |
| n | 3 | 3 | 3 |
| $C_{max}$ (ng/mL) | 3740 | 3927 | 4637 |
| $T_{max}$ (h) | 0.5 | 1.0 | 0.5 |
| $AUC_{0-inf}$ (ng·h/mL) | 7086 | 23798 | 12618 |
| Half life ($t_{1/2}$) (h) | 2.0 | 2.8 | 2 |
| Oral bioavailability (%) | 78 | 90 | 89 |

E.4 In Vivo Efficacy

The concept of studying the in vivo effect of an antibacterial compound by treating intraperitoneally infected mice was introduced in 1911 for optochin against pneumococci (Morgenroth and Levy, 1911). The popularity of the model comes from the ease of its use with short-duration experiments, reproducible infections and simple end-points.

Method

Methicillin-sensitive S. aureus strain ATCC 29213 is used to infect female Swiss albino mice. A Brain Heart Infusion (BHI) broth bacterial culture is inoculated the day before infection, incubated at 37° C. overnight and diluted in fresh BHI broth to the desired concentration. Intraperitoneal (i.p.) injection of ~$5 \times 10^9$ colony forming units (CFU) is performed in either of the lateral lower quadrants of the abdomen. After inoculation, mice are kept in their cages under daily observation for development of signs of infection or death. For the treatment of mice, both the p.o. and i.v. routes may be used and each mouse is treated individually by gavage or by i.v. injection. Both solutions and suspensions are tested in this model. The parameter used for monitoring the course of infection and the effect of treatment is death or survival of the animals over 3 days post-infection. As death could also be due to toxic side effects, a non-infected control group of 3 mice, treated with the highest dose of the compound tested, is included.

Results

Compounds of the invention/examples display good in vivo efficacy properties, for instance compounds may exhibit such properties as measured by % survival (following the above test).

The invention claimed is:

1. A compound of formula (I):

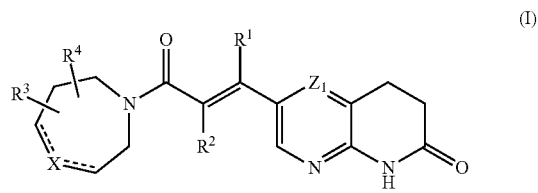

wherein
$Z_1$ represents CH or N;
$R^1$ is hydrogen, $C_{1-4}$alkyl or halo;

$R^2$ is hydrogen, $C_{1-4}$alkyl or halo;
$R^3$ is hydrogen;
$R^4$ is hydrogen, $C_{1-6}$alkyl, halo, aryl, heteroaryl, $C_{1-6}$alkyl substituted with aryl, or $C_{1-6}$alkyl substituted with heteroaryl;
aryl is phenyl or phenyl substituted with one, two or three substituents each individually selected from the group consisting of halo, hydroxy, $C_{1-4}$alkyl, polyhalo$C_{1-4}$alkyl, $C_{1-4}$alkyloxy, polyhalo$C_{1-4}$alkyloxy, cyano, nitro and amino;
heteroaryl is furanyl, thiophenyl, pyrrolyl, pyrazolyl, imidazolyl, isoxazolyl, triazolyl, triazolyl, tetrazolyl, isothiazolyl, thiadiazolyl, oxadiazolyl, pyridinyl, pyridazinyl, pyrimidinyl, pyrazinyl, benzo[1,3]dioxolyl, benzofuranyl, benzothiazolyl, indolyl, 2,3-dihydro-1H-indolyl, tetrahydrothiophenyl, or quinolinyl;
wherein each heteroaryl may be substituted with one or two substituents each independently selected from the group consisting of halo, cyano, $C_{1-4}$alkyl, $C_{1-4}$alkyloxy, $C_{1-4}$ alkylcarbonyl, and phenyl;
wherein the X-containing ring represents:

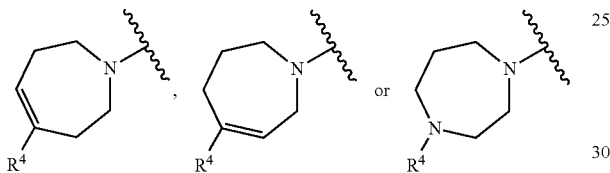

or a pharmaceutically acceptable acid addition salt thereof.

2. A compound as claimed in claim 1 wherein:
$Z_1$ represents CH;
$R^1$ is hydrogen or $C_{1-4}$alkyl; and
$R^2$ is hydrogen or $C_{1-4}$alkyl.

3. A compound as claimed in claim 1 wherein
$R^1$ is hydrogen;
$R^2$ is hydrogen;
$R^4$ is halo, aryl, heteroaryl, or $C_{1-6}$alkyl substituted with aryl;
aryl is phenyl or phenyl substituted with one or two substituents each individually selected from the group consisting of halo, $C_{1-4}$alkyl, polyhalo$C_{1-4}$alkyl, $C_{1-4}$alkyloxy and polyhalo$C_{1-4}$alkyloxy; and
heteroaryl is thiophenyl, pyrrolyl, triazolyl or triazolyl.

4. A compound as claimed in claim 1 wherein $R^1$ is hydrogen and $R^2$ is hydrogen.

5. A compound as claimed in claim 1 wherein $R^4$ is aryl.

6. A compound as claimed in claim 1 wherein $R^4$ is heteroaryl.

7. A compound as claimed in claim 1 wherein $R^4$ is $C_{1-6}$alkyl substituted with aryl.

8. A pharmaceutical composition comprising a pharmaceutically acceptable carrier and a therapeutically active amount of a compound as claimed in claim 1.

9. A process for preparing a pharmaceutical composition wherein a therapeutically active amount of a compound as claimed in claim 1 is intimately mixed with a pharmaceutically acceptable carrier.

10. A method of treatment of a subject suffering from a bacterial infection, comprising administering to the subject an effective amount of a compound of formula (I) as claimed in claim 1.

11. A method of treatment as claimed in claim 10 wherein the bacterial infection is caused by a bacterium that expresses a FabI enzyme.

12. A process for preparing a compound of formula (I), as claimed in claim 1, comprising
(i) reacting an intermediate of formula (II) with an intermediate of formula (III),

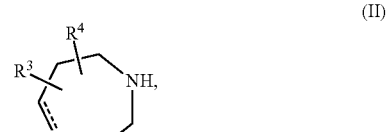

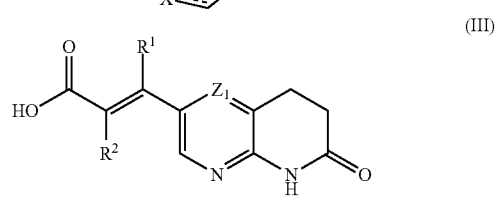

or
(ii) reacting an intermediate of formula (V) with an intermediate of formula (VI),

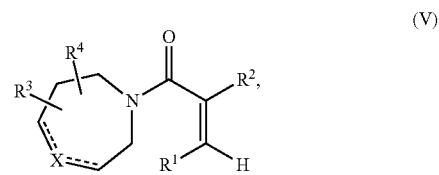

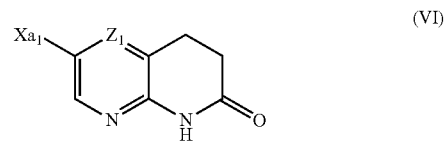

wherein $Xa_1$ represents a suitable leaving group.

* * * * *